United States Patent [19]

Sunagawa et al.

[11] Patent Number: 5,750,686

[45] Date of Patent: May 12, 1998

[54] CARBAPENEM COMPOUNDS AND PROCESS FOR PRODUCING THE SAME

[75] Inventors: Makoto Sunagawa, Itami; Hiroshi Yamaga, Osaka; Yoshihiro Sumita, Nara-ken, all of Japan

[73] Assignee: Sumitomo Pharmaceuticals Company, Limited, Osaka-fu, Japan

[21] Appl. No.: 564,032

[22] PCT Filed: Jun. 14, 1994

[86] PCT No.: PCT/JP94/00958

§ 371 Date: Dec. 14, 1995

§ 102(e) Date: Dec. 14, 1995

[87] PCT Pub. No.: WO94/29313

PCT Pub. Date: Dec. 22, 1994

[30] Foreign Application Priority Data

Jun. 16, 1993 [JP] Japan ................................ 5-171073

[51] Int. Cl.$^6$ ........................ C07D 487/04; A61K 31/40
[52] U.S. Cl. .............................. 540/350; 514/210
[58] Field of Search ................................ 540/350

[56] References Cited

U.S. PATENT DOCUMENTS

| | | | |
|---|---|---|---|
| 4,840,946 | 6/1989 | Häbich et al. | 514/210 |
| 5,153,187 | 10/1992 | Iwasaki | 514/210 |
| 5,519,015 | 5/1996 | Jung | 540/350 |

FOREIGN PATENT DOCUMENTS

| | | |
|---|---|---|
| 0010317 | 4/1980 | European Pat. Off. . |
| 0017992 | 10/1980 | European Pat. Off. . |
| 0071908 | 2/1983 | European Pat. Off. . |
| 0160876 | 11/1985 | European Pat. Off. . |
| 61-5081 | 1/1986 | Japan . |
| 63-63680 | 3/1988 | Japan . |

Primary Examiner—Mukund J. Shah
Assistant Examiner—P. K. Sripada
Attorney, Agent, or Firm—Birch, Stewart, Kolasch & Birch, LLP

[57] ABSTRACT

A novel β-lactam compound of the formula [1]:

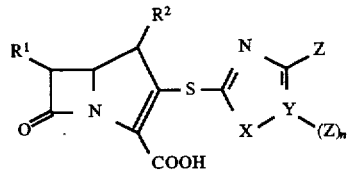

or a pharmaceutically acceptable salt thereof, which shows an excellent antibacterial activity against Gram-positive bacteria, especially against methicillin-resistant staphylococci and methicillin-resistant coagulase-negative staphylococci, and a process for producing the same. $R_1$, $R_2$, X, Y, Z are as defined in the specifacation.

7 Claims, No Drawings

CARBAPENEM COMPOUNDS AND PROCESS FOR PRODUCING THE SAME

This Application is a 371 of PCT/JP94/00958 Jun. 14 1994

TECHNICAL FIELD

The present invention relates to a novel β-lactam compound of the formula [1] as mentioned below.

BACKGROUND ART

By the wide clinical application of the third-generation cephalosporin drugs, gram-positive bacteria have become to be frequently isolated. Particularly, methicillin-resistant staphylococci (hereinafter referred to as MRSA) is recently frequently isolated, and becomes a serious problem in clinical field, because infectious diseases caused by MRSA are difficult to be treated. For example, vancomycin, which has been broadly used for infectious diseases caused by MRSA recently, is difficult to be administered because of its side effects, and glycopeptide-resistant bacteria are expected to be increased in future by administration thereof. Moreover, it has recently been reported the increase in isolation of methicillin-resistant coagulase-negative staphylococci (MRCNS). Under these circumstances, it has been desired to develop a safe drug having a strong anti-MRSA activity and anti-MRCNS activity.

An object of the present invention is to provide a β-lactam drug having an excellent antibacterial activity against Gram-positive bacteria, especially against MRSA and MRCNS.

DISCLOSURE OF THE INVENTION

The present inventors have intensively studied, and have found that a compound of the following formula [1] shows a strong effect on Gram-positive bacteria, and shows an excellent antibacterial activity especially against MRSA and MRCNS, and have accomplished the present invention.

That is, the present invention relates to a compound of the formula [1]:

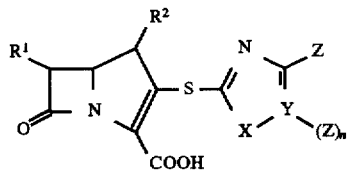

wherein $R^1$ is a lower alkyl group or a lower alkyl group substituted by a hydroxy group, $R^2$ is a hydrogen atom or a lower alkyl group, X is an oxygen atom, a sulfur atom or NH, Y is a nitrogen atom or a carbon atom, n is 0 when Y is a nitrogen atom, or n is 1 when Y is a carbon atom, Zs are each independently a) a hydrogen atom; b) $R^a$ ($R^a$ is a lower alkyl group, a substituted lower alkyl group or a substituted lower alkenyl group); c) A (A is an aryl group, a substituted aryl group or a 5- to 6-membered cyclic amino group); d) —OH or —OP$^a$ (P$^a$ is a protecting group for hydroxy group); e) —OR$^a$ (R$^a$ is the same as defined above); f) —OA (A is the same as defined above); g) —SR$^a$ (R$^a$ is the same as defined above); h) —SA (A is the same as defined above); i) —NH$_2$ or —NHP$^b$ (P$^b$ is a protecting group for amino group); j) —NHR$^a$, —N(R$^b$)R$^c$ or —N(R$^a$)P$^b$ (R$^a$ and P$^b$ are the same as defined above, R$^b$ and R$^c$ are a lower alkyl group or a substituted lower alkyl group, or R$^b$ and R$^c$ may combine together with the nitrogen atom to form a 3- to 7- membered heterocyclic group, said heterocyclic group optionally containing other 1 or 2 heteroatoms selected from an oxygen atom, a sulfur atom and a nitrogen atom, and having optionally a substituent); k) —NHA or —N(A)P$^b$ (A and P$^b$ are the same as defined above); l) —N(R$^a$)A (A and R$^a$ are the same as defined above); m) —CONH$_2$; n) —CONHR$^a$, —CON(R$^b$)R$^c$ (R$^a$, R$^b$ and R$^c$ are the same as defined above); o) —CONHA (A is the same as defined above); p) —CON(R$^a$)A (A and R$^a$ are the same as defined above); q) —CONHC(NH)NH$_2$ or —CONHC(NP$^b$)NHP$^b$ (P$^b$ is the same as defined above); r) —COOH or —COOP$^c$ (P$^c$ is a protecting group for carboxyl group); s) —COOR$^a$ (R$^a$ is the same as defined above); t) —COOA (A is the same as defined above); u) —COR$^a$ (R$^a$ is the same as defined above); v) —COA (A is the same as defined above); w) a halogen atom; or x) a cyano group, or a pharmaceutically acceptable salt thereof or a non-toxic ester thereof.

Further, the present invention relates to a process for producing a novel β-lactam compound of the formula [1]:

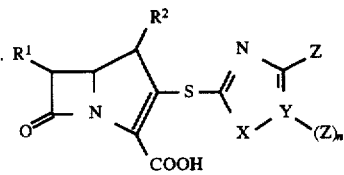

or a pharmaceutically acceptable salt thereof or a non-toxic ester thereof, which comprises reacting a compound of the formula [2]:

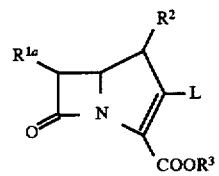

wherein $R^2$ is the same as defined above, $R^{1a}$ is a lower alkyl group, a lower alkyl group substituted by a hydroxy group, or a lower alkyl group substituted by a hydroxy group protected by a protecting group, $R^3$ is a protecting group for carboxyl group, L is an active ester of hydroxy group, with a compound of the formula [3]:

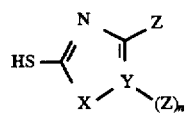

wherein X, Y, Z and n are the same as defined above, in the presence of a base, or reacting the compound of the formula [2] with a thiolate salt of the compound of the formula [3] to give a compound of the formula [4]:

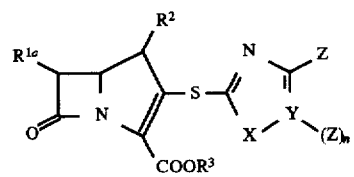

wherein $R^{1a}$, $R^2$, $R^3$, X, Y, Z and n are the same as defined above, followed by removing the protecting group for hydroxy group for $R^{1a}$ and/or removing the protecting group for carboxyl group represented by $R^3$.

The lower alkyl group for $R^1$, $R^{1a}$ and $R^2$ in the above formulae [1] and [2] includes ones having 1 to 5 carbon atoms, for example, methyl, ethyl, n-propyl, isopropyl, n-butyl, isobutyl, tert-butyl, n-pentyl, etc.

The lower alkyl group substituted by a hydroxy group for $R^1$ and $R^{1a}$ includes ones having 1 to 5 carbon atoms, for example, hydroxymethyl, 1hydroxyethyl, 2-hydroxyethyl, 1-hydroxy-1-methylethyl, 1-hydroxypropyl, 2hydroxypropyl, and the like.

The heterocyclic group of the formula:

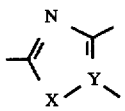

includes, for example, thiazole, 1,2,4-thiadiazole, oxazole, imidazole, 1,2,4-triazole, 1,2,4-oxadiazole, etc.

The lower alkyl group for $R^a$, $R^b$ and $R^c$ in Z includes a straight chain, branched chain or cyclic alkyl having 1 to 6 carbon atoms, for example, methyl, ethyl, n-propyl, n-butyl, isopropyl, isobutyl, cyclopropyl, cyclopentyl, cyclohexyl, etc.

The lower alkenyl group includes ones having 2 to 6 carbon atoms, for example, vinyl, propenyl, butenyl, pentenyl, hexenyl, etc.

The substituent on the substituted lower alkyl group or the substituted lower alkenyl group of the present invention includes, for example, an aryl group, a substituted aryl group, a hydroxy group, a lower alkoxy group, a lower alkoxy group substituted by a hydroxy group or an amino group, a lower alkylcarbonyloxy group, a lower alkoxycarbonyl group, an amino group, a mono- or di-lower alkyl-substituted amino group (said lower alkyl group may optionally have a substituent selected from an aminocarbonyl group having optionally a lower alkyl substituent, a hydroxy group, a carboxyl group and a lower alkylcarbonyl group), a guanidino group, a tri(lower alkyl) ammonium group (said lower alkyl group may optionally have a substituent selected from an aminocarbonyl group having optionally a lower alkyl substituent, a hydroxy group, a carboxyl group and a lower alkylcarbonyl group), a carboxyl group, an aminocarbonyl group, a mono- or di-(lower alkyl)aminocarbonyl group (said lower alkyl group may optionally have a substituent selected from an aminocarbonyl group having optionally a lower alkyl substituent, a hydroxy group, a carboxyl group and a lower alkylcarbonyl group), a halogen atom, a cyano group, an alkylamidino group having 1 to 3 carbon atoms, a guanidinocarbonyl group, etc. These substituents may optionally be protected by an appropriate protecting group. The positions of these substituents may be any position which is chemically possible, and the substitution either at one position or at more positions is available.

The 3- to 7-membered heterocyclic group represented by —N($R^b$)$R^c$ includes, for example, aziridinyl, azetidinyl, pyrrolidinyl, piperidinyl, piperazinyl, homopiperazinyl, imidazolinyl, imidazolidinyl, morpholinyl, thiamorpholinyl, etc. The substituent on said heterocyclic group includes, for example, a lower alkyl group, or a lower alkyl group substituted by an aminocarbonyl group being optionally substituted by a lower alkyl group, a hydroxy group, a carboxyl group or a lower alkylcarbonyl group, such as aminocarbonylmethyl, a lower alkylaminocarbonylmethyl group, 2-hydroxyethyl group, etc. Moreover, these 3- to 7-membered heterocyclic groups also include ones wherein the nitrogen atom thereof is made quaternary by the same lower alkyl group or the same substituted lower alkyl group as the substituents on the above-mentioned heterocyclic groups.

The aryl group includes both a carbocyclic aryl group and a heterocyclic aryl group, for example, groups derived from aromatic hydrocarbons and heterocyclic compounds such as benzene, pyridine, pyrimidine, pyrazine, furan, pyrrole, thiophene, imidazole, triazole, tetrazole, oxazole, thiazole, thiadiazole, naphthalene, quinoline, isoquinoline, quinoxaline, benzofuran, indole, benzothiophene, benzimidazole, benzoxazole, benzothiazole, etc.

The substituent on the substituted aryl group includes, for example, a lower alkyl group, an aminocarbonyl-lower alkyl group having optionally a lower alkyl substituent, a hydroxy-lower alkyl group, a carboxyl-lower alkyl group, a lower alkylcarbonyl-lower alkyl group, a hydroxy group, a lower alkoxy group, an amino group, a mono- or di-(lower alkyl)amino group, a tri(lower alkyl)ammonium group, a formylamino group, a formimide group, an acetimido group, an aminocarbonyl group, an alkylaminocarbonyl group represented by —CONHR$^a$ or —CON($R^b$)$R^c$ ($R^a$, $R^b$ and $R^c$ are the same as defined above), a guanidinocarbonyl group, a nitro group, a halogen atom, a cyano group, a carboxyl group, a sulfonamide group, a 5- to 7-membered saturated heterocyclic group having one or more nitrogen atoms, a heterocyclic aryl group, a quaternary heterocyclic aryl group, etc. These substituents may be protected by an appropriate protecting group. The positions of the substituents may be any one which is chemically possible, and the substitution either at one position or more positions is also available. Moreover, when the substituted aryl group is a nitrogen-containing heterocyclic aryl group, said aryl group also includes ones wherein the nitrogen atom therein is made quaternary by a lower alkyl group, a substituted lower alkyl group, a hydroxy group, an amino group, for example, pyridinium, pyrimidinium, isoquinolinium, thiazolium, imidazolium, etc.

The 5- to 6-membered cyclic amino group includes, for example, pyrrolidine, dihydropyrrole, piperidine, tetrahydropyridine, etc. The nitrogen atom of said cyclic amino group may be substituted by 1) a lower alkyl group, or 2) a lower alkyl group substituted by an aminocarbonyl group, a lower alkyl-substituted aminocarbonyl group, a hydroxy group, a carboxyl group, or a lower alkylcarbonyl group.

The protecting group for carboxyl group represented by $P^c$ for Z of the above formula [1], and the protecting group for carboxyl group represented by $R^3$ of the above formula [2] may be any conventional ones, but preferably a straight chain or branched chain lower alkyl group having 1 to 5 carbon atoms such as methyl, ethyl, isopropyl, tert-butyl, etc., a halogeno-lower alkyl group having 1 to 5 carbon atoms such as 2-iodoethyl, 2,2,2-trichloroethyl, etc., a lower alkoxymethyl group having 1 to 5 carbon atoms such as methoxymethyl, ethoxymethyl, isobutoxymethyl, etc., a lower aliphatic acyloxymethyl group having 1 to 5 carbon atoms such as acetoxymethyl, propionyloxymethyl, butyryloxymethyl, pivaloyloxymethyl, etc., a 1-($C_1$–$C_5$)-lower alkoxycarbonyloxyethyl group such as 1-ethoxycarbonyloxyethyl, etc., an aralkyl group being optionally substituted by a lower alkoxy group or a nitro group such as benzyl, p-methoxybenzyl, o-nitrobenzyl, p-nitrobenzyl, etc., a lower alkenyl group having 3 to 7 carbon atoms such as allyl, 3-methylallyl, etc., a benzhydryl, or a phthalidyl group, and the like.

Besides, the protecting group for hydroxy group represented by $P^a$ for Z of the formula [1], the protecting group for hydroxy group represented by $R^{1a}$ of the formula [2], and the protecting group for amino group represented by $P^b$ for Z may be any conventional protecting groups, but preferably a lower alkoxycarbonyl group having 1 to 5 carbon atoms such as tert-butyloxycarbonyl group, a halogenoalkoxycarbonyl group having 1 to 5 carbon atoms such as 2-iodoethyloxycarbonyl group, 2,2,2-trichloroethyloxycarbonyl group, etc., a substituted or unsubstituted lower alkenyloxycarbonyl group having 3 to 7 carbon atoms such as allyloxycarbonyl group, etc., a substituted or unsubstituted aralkyloxycarbonyl group such as benzyloxycarbonyl, p-methoxybenzyloxycarbonyl, o-nitrobenzyloxycarbonyl, p-nitrobenzyloxycarbonyl, etc., a trialkylsilyl group such as trimethylsilyl, triethylsilyl, tertbutyldimethylsilyl, etc.

The halogen atom is fluorine, chlorine, bromine, etc.

The pharmaceutically acceptable salt of the compound of the formula [1] is a conventional non-toxic salt. For example, the salt with the carboxylic acid of the formula [1] is, for example, a salt with an inorganic base such as sodium, potassium, calcium, magnesium, ammonium, etc., a salt with an organic base such as triethylammonium, pyridinium, diisopropylammonium, etc., or an inner salt formed with a cation such as a quaternary ammonium ion at the 3- side chain. The salt with a basic group of the formula [1] is, for example, a salt with an inorganic acid such as hydrochloric acid, sulfuric acid, phosphoric acid, etc., or a salt with an organic acid such as formic acid, acetic acid, oxalic acid, methanesulfonic acid, benzenesulfonic acid, etc.

The non-toxic ester of the compound of the formula [1] is a conventional pharmaceutically acceptable ester at the 2-carboxyl group of the carbapenem antibacterial agents, for example, esters which are easily hydrolyzed in vivo such as acetoxymethyl ester, pivaloyloxymethyl ester, 1-(ethoxycarbonyloxy) ethyl ester, phthalidyl ester, etc.

Among the compounds of the present invention, preferred compounds are compounds of the formula [1-a]:

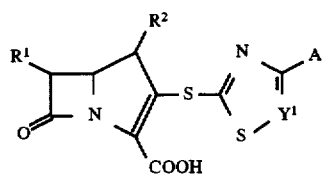

wherein $R^1$, $R^2$ and A are the same as defined above, and $Y^1$ is N or CH, or a pharmaceutically acceptable salt thereof.

Other preferred compounds of the present invention are compounds of the formula [1] wherein X is a sulfur atom, and Y is CH, or a pharmaceutically acceptable salt thereof.

The preferred groups for Z are, for example, a lower alkyl group, a phenyl group, a substituted phenyl group, a heterocyclic aryl group, a substituted heterocyclic aryl group, an aminocarbonyl group, a mono- or di-(lower alkly) aminocarbonyl group, a substituted or unsubstituted heterocyclic arylcarbonyl group, an amino-lower alkyl group, a mono- or di-(lower alkyl) amino-lower alkyl group, a hydroxy-lower alkyl group, a lower alkoxycarbonyl-lower alkyl group.

The heterocyclic aryl group for the preferred groups for Z includes, for example, pyridyl, thienyl, furyl, quinolyl, etc., and these groups may optionally be substituted by a group selected from a lower alkyl group, an amino group, an aminocarbonyl-lower alkyl group, a mono- or di-(lower alkyl)aminocarbonyl-lower alkyl group and a hydroxy group.

The substituted phenyl group for the preferred groups for Z includes, for example, a phenyl group substituted by a group selected from an aminocarbonyl group, a mono- or di-(lower alkyl)aminocarbonyl group (said lower alkyl group optionally being substituted by an amino group or a mono- or di-(lower alkyl)amino group), a 4-(lower alkyl or aminocarbonyl-lower alkyl or a mono- or di-(lower alkyl) aminocarbonyl-lower alkyl)piperazinylcarbonyl group, a piperidinylcarbonyl group, a pyridyl-lower alkyl group, a lower alkylsubstituted imidazolyl-lower alkyl group, a piperidinyl-lower alkyl group, a 4-(lower alkyl) or aminocarbonyl-lower alkyl or a mono- or di-(lower alkyl) aminocarbonyl-lower alkyl)piperazinyl-lower alkyl group, an amino-lower alkyl group and a mono-or di-(lower alkyl) amino-lower alkyl group.

The process for producing the present compounds is explained in detail below.

The compound of the formula [4]:

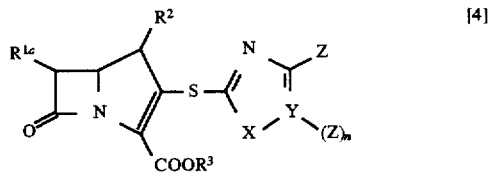

wherein $R^{1a}$, $R^2$, $R^3$, X, Y, Z and n are the same as defined above, is prepared by reacting a reactive ester compound of the formula [2]:

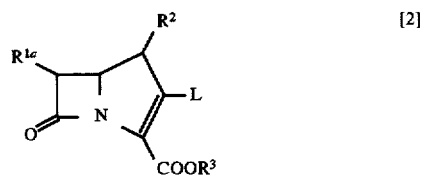

wherein $R^2$, $R^{1a}$, $R^3$ and L are the same as defined above, with a mercaptan compound of the formula [3]:

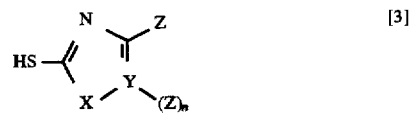

wherein X, Y, Z and n are the same as defined above, in the presence of a base in an inert solvent, or by reacting the compound of the formula [2] with a thiolate salt of the compound of the formula [3] in an inert solvent.

The active ester for hydroxy group includes, for example, a substituted or unsubstituted benzenesulfonic acid ester such as benzenesulfonic acid ester, p-toluenesulfonic acid ester, p-nitrobenzenesulfonic acid ester, p-bromobenzenesulfonic acid ester, etc., a lower alkanesulfonic acid ester having 1 to 5 carbon atoms such as methanesulfonic acid ester, ethanesulfonic acid ester, etc., a halogenoalkanesulfonic acid ester having 1 to 5 carbon atoms such as trifluoromethanesulfonic acid ester, etc., diphenylphosphoric acid ester, a halide compound such as chloride, bromide, iodide, etc., which is an ester with a hydrohalogenic acid. Among these reactive esters for hydroxy group, the preferred esters are, for example, p-toluenesulfonic acid ester, methanesulfonic acid ester, trifluoromethanesulfonic acid ester and diphenylphosphoric acid ester.

The inert solvent used in the reaction of the compound of the formula [2] and the compound [3] in the presence of a base to give the compound [4] includes, for example, dioxane, tetrahydrofuran, dimethylsulfoxide, dimethylformamide, acetonitrile, benzene, toluene, hexamethylphosphoramide, or a mixture thereof.

The base includes, for example, inorganic bases such as sodium carbonate, potassium carbonate, sodium hydride, potassium hydride, and organic bases such as pyridine, dimethylaminopyridine, triethylamine, diisopropylethylamine, 1,8-diazabicyclo[5.4.0]undec-7-ene (DBU). The more preferable one is DBU. The base is used in an amount enough to proceed the reaction well, and is usually used in an amount of 1 to 3 equivalents, to 1 equivalent of the mercaptan compound of the formula [3].

The mercaptan compound of the formula [3] is used in an amount enough to proceed the reaction well, and can be used in an excess amount, but usually used in an amount of 1 to 2 equivalents, to 1 equivalent of the compound of the formula [2].

The reaction is carried out at a temperature from −78° C. to +600° C., but is preferably carried out at a temperature from −40° C. to +40° C. After the reaction is complete, the product can be isolated from the reaction mixture by a conventional organic chemical method.

The inert solvent used in the reaction of the compound of the formula [2] and a thiolate salt of the compound [3] to give the compound [4] includes, for example, dioxane, tetrahydrofuran, dimethylsulfoxide, dimethylformamide, acetonitrile, benzene, toluene, hexamethylphosphoramide, or a mixture of these solvents.

The thiolate salt is used in an amount enough to proceed the reaction well, and may be used in an excess amount, but usually used in an amount of 1 to 2 equivalents, to 1 equivalent of the compound of the formula [2].

The reaction is carried out at a temperature from −78° C. to +60° C., preferably at a temperature from −40° C. to +40° C. After the reaction is complete, the product can be isolated by a conventional organic chemical method.

The thiolate salt is prepared from the mercaptan compound of the formula [3] and a base. The base includes, for example, inorganic bases such as sodium hydride, potassium hydride, etc., metal alkoxides such as tert-butoxy potassium, sodium methoxide, etc., and metal amides such as sodium amide, lithium diisopropylamide, lithium disilazide, etc.

The β-lactam compound of the formula [1] can be prepared from the above obtained compound of the formula [4], if necessary, by carrying out a combination of the removal of the protecting group for hydroxy group of $R^{1a}$ and the removal of the protecting group for carboxyl group represented by $R^3$, by a conventional method, or by simultaneously carrying out the removal of both protecting groups.

The removal of these protecting groups may be carried out by a conventional method such as treatment with an acid, a base, or a reducing agent, for example, by the methods disclosed in T. W. Greene: Protective Groups in Organic Synthesis, J. Wiley & Sons Inc., 1981. The acid is preferably trifluoroacetic acid, formic acid, boron trifluoride, aluminum chloride, etc., or a mixture thereof. The base is preferably alkali metal carbonates such as sodium carbonate, potassium carbonate, etc., alkali metal sulfides such as sodium sulfide, potassium sulfide, etc., or ammonium tetrabutylfluoride. When the treatment using a reducing agent is employed, it is preferably hydrogenolysis using zinc and acetic acid, or hydrogen and palladium-carbon or platinum. There may be also used palladium [0] compound.

The solvent used therein may be any one which does not disadvantageously affect the reaction, but it is preferably water, alcohols (e.g. methanol, ethanol, etc.), ethers (e.g. tetrahydrofuran, dioxane, etc.), fatty acids (e.g. acetic acid, etc.), or a mixture thereof. The reaction is possibly controlled by cooling or heating the reaction system. The reaction is usually carried out at a temperature from −30° C. to +40° C. After the reaction is complete, the product can be isolated from the reaction mixture by a conventional organic chemical method. For example, the reaction mixture is neutralized and it is subjected to column chromatography using an adsorbent resin, and then, the required fractions are combined, lyophilized to give the product.

Before, or after, or simultaneously the above mentioned removal of the protecting groups, the desired compounds may be obtained by a combination of the conversion reactions of the groups represented by Z of the formula [4] or [1]. The conversion reaction thereof is, for example, the removal of the protecting groups, the imidoylization reaction of the amino group, the reaction of making quaternary the heterocyclic aryl group, the oxidization reaction, the reduction reaction, etc.

The compound of the formula [2] is a known compound, for example, disclosed in Japanese Patent Second Publication (KOKOKU) No. 55514/1988.

The mercaptan compound of the formula [3] may be prepared by various conventional methods, for example, by methods disclosed in K. Hofmann, Heterocyclic Chemistry, vol. 6 (1953), J. V. Metzger, ibid., vol. 34 (1979), I. J. Turchi, ibid., vol. 45 (1986), Interscience Publishers, Inc. or A. R. Katritzky, Advances in Heterocyclic Chemistry, vol. 32 (1982), Academic Press, or by a combination of these methods.

The compound of the above formula [1] has optical isomers based on asymmetric carbon atoms at the 4-, 5- and 6-positions of the carbapenem nucleus as shown in the following formula;

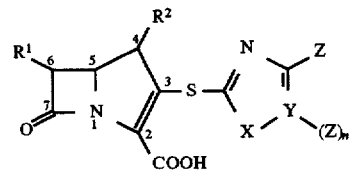

wherein $R^1$, $R^2$, X, Y, Z and n are the same as defined above. These optical isomers are conveniently expressed by a single formula, but the present invention should not be construed to be limited thereto, but included all the isomers based on each asymmetric carbon atom as well as a mixture thereof.

However, the preferable compounds are compounds of the formula [1] wherein the 5-carbon atom has R-configuration, such as (5R,6R)-compound or (5R,6S)-compound, when $R^2$ is a hydrogen atom. When $R^2$ is a lower alkyl group, the preferable compounds are compounds of the formula [1] wherein the 4-carbon atom has R-configuration, and the 5-carbon atom has S-configuration, such as (4R,5S,6S)-compound, or (4R,5S,6R)-compound.

Moreover, when $R^1$ is 1-hydroxyethyl group, the compounds of the present invention have isomers based on the 8-carbon atom, i.e. the 8-carbon atom is R-configuration or S-configuration, as shown in the following formula, and the preferable one is the compound wherein the 8-carbon atom has R-configuration.

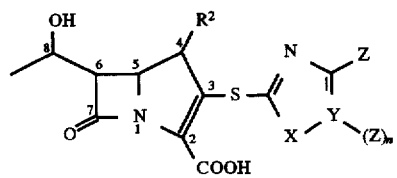

wherein $R^2$, X, Y, Z and n are the same as defined above.

When preparing the isomers having such a configuration, there is used a corresponding isomer of the compound of the formula [2].

The compounds of the present invention of the above formula [1] are novel β-lactam compounds having an azole-thio group having various substituents at the 3-position of the carbapenem nucleus. These compounds show an excellent antibacterial activity and are useful as a medicament.

The representative examples of the compounds of the formula [1] of the present invention are shown in Table 1.

TABLE 1

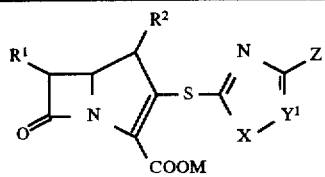

| Comp. No. | $R^1$ | $R^2$ | X | $Y^1$ | Z |
|---|---|---|---|---|---|
| 1 | $CH_3CH(OH)-$ | Me | S | CH | —C₆H₄—C(O)—N(piperazine)NMe |
| 2 | $CH_3CH(OH)-$ | Me | S | CH | —C₆H₄—C(O)—N(piperazine)N⁺Me₂ |
| 3 | $CH_3CH(OH)-$ | Me | S | CH | —C₆H₄—C(O)—N(piperazine)N⁺(Me)(CH₂CONH₂) |
| 4 | $CH_3CH(OH)-$ | Me | S | CH | —C₆H₄—C(O)—N(piperazine)N⁺(Me)(CH₂CONMe₂) |
| 5 | $CH_3CH(OH)-$ | Me | S | CH | —C₆H₄—C(O)—NH—CH₂CH₂—NH₂ |
| 6 | $CH_3CH(OH)-$ | Me | S | CH | —C₆H₄—C(O)—NH—CH₂CH₂—NMe₂ |
| 7 | $CH_3CH(OH)-$ | Me | S | CH | —C₆H₄—C(O)—NH—CH₂CH₂—N⁺Me₃ |
| 8 | $CH_3CH(OH)-$ | Me | S | CH | m-C₆H₄—C(O)—N(piperazine)NMe |
| 9 | $CH_3CH(OH)-$ | Me | S | CH | m-C₆H₄—C(O)—N(piperazine)N⁺Me₂ |
| 10 | $CH_3CH(OH)-$ | Me | S | CH | m-C₆H₄—C(O)—N(piperazine)N⁺(Me)(CH₂CONH₂) |

TABLE 1-continued

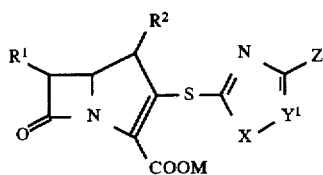

| Comp. No. | R¹ | R² | X | Y¹ | Z |
|---|---|---|---|---|---|
| 11 | CH₃CH(OH)— | Me | S | CH | 3-methylbenzoyl-piperazine-N⁺(Me)(CH₂CONMe₂) |
| 12 | CH₃CH(OH)— | Me | S | CH | 3-methyl-C(O)NH-CH₂CH₂-NH₂ |
| 13 | CH₃CH(OH)— | Me | S | CH | 3-methyl-C(O)NH-CH₂CH₂-NMe₂ |
| 14 | CH₃CH(OH)— | Me | S | CH | 3-methyl-C(O)NH-CH₂CH₂-N⁺Me₃ |
| 15 | CH₃CH(OH)— | Me | S | CH | 4-methylbenzyl-CH₂OH (para) |
| 16 | CH₃CH(OH)— | Me | S | CH | 3-methylbenzyl-CH₂OH (meta) |
| 17 | CH₃CH(OH)— | Me | S | CH | 4-methylbenzyl-pyridinium |
| 18 | CH₃CH(OH)— | Me | S | CH | 4-methylbenzyl-(N-methylimidazolium) |
| 19 | CH₃CH(OH)— | Me | S | CH | 4-methylbenzyl-(N-methylpiperidinium) |

TABLE 1-continued

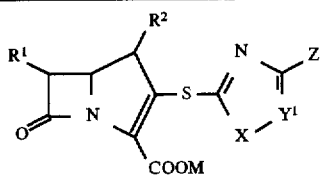

| Comp. No. | R¹ | R² | X | Y¹ | Z |
|---|---|---|---|---|---|
| 20 | CH₃CH(OH)— | Me | S | CH | 4-(4-methylpiperazin-1-ylmethyl)phenyl |
| 21 | CH₃CH(OH)— | Me | S | CH | 4-(aminomethyl)phenyl |
| 22 | CH₃CH(OH)— | Me | S | CH | 4-(dimethylaminomethyl)phenyl |
| 23 | CH₃CH(OH)— | Me | S | CH | 4-(2-aminoethyl)phenyl |
| 24 | CH₃CH(OH)— | Me | S | CH | 4-(2-dimethylaminoethyl)phenyl |
| 25 | CH₃CH(OH)— | Me | S | CH | 4-(2-trimethylammonioethyl)phenyl |
| 26 | CH₃CH(OH)— | Me | S | CH | 3-(pyridinio-1-ylmethyl)phenyl |
| 27 | CH₃CH(OH)— | Me | S | CH | 3-(3-methylaminoiminio-methyl)phenyl |
| 28 | CH₃CH(OH)— | Me | S | CH | 3-(aminomethyl)phenyl |
| 29 | CH₃CH(OH)— | Me | S | CH | 3-(dimethylaminomethyl)phenyl |
| 30 | CH₃CH(OH)— | Me | S | CH | 3-(2-aminoethyl)phenyl |

TABLE 1-continued
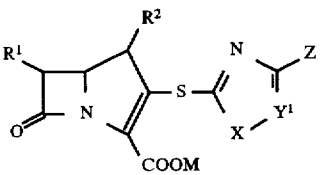
| Comp. No. | R¹ | R² | X | Y¹ | Z |
|---|---|---|---|---|---|
| 31 | CH₃CH(OH)— | Me | S | CH | 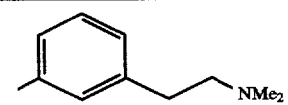 |
| 32 | CH₃CH(OH)— | Me | S | CH | 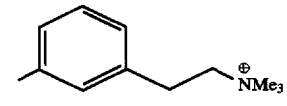 |
| 33 | CH₃CH(OH)— | Me | S | CH | 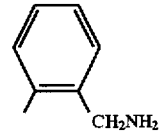 |
| 34 | CH₃CH(OH)— | Me | S | CH | 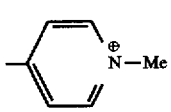 |
| 35 | CH₃CH(OH)— | Me | S | CH | 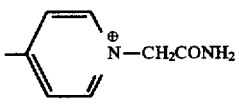 |
| 36 | CH₃CH(OH)— | Me | S | CH | 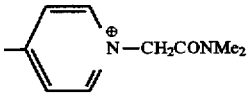 |
| 37 | CH₃CH(OH)— | Me | S | CH | 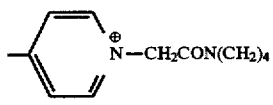 |
| 38 | CH₃CH(OH)— | Me | S | CH | 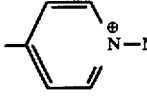 |
| 39 | CH₃CH(OH)— | Me | S | CH | 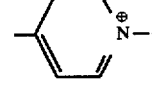 |
| 40 | CH₃CH(OH)— | Me | S | CH | 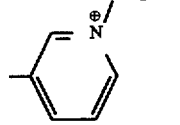 |
| 41 | CH₃CH(OH)— | Me | S | CH | 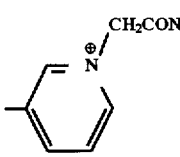 |

TABLE 1-continued

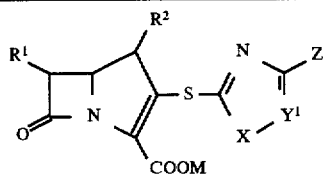

| Comp. No. | R¹ | R² | X | Y¹ | Z |
|---|---|---|---|---|---|
| 42 | CH₃CH(OH)— | Me | S | CH | (1-methylpyridinium-2-yl) |
| 43 | CH₃CH(OH)— | Me | S | CH | (5-carbamoylthiophen-2-yl) |
| 44 | CH₃CH(OH)— | Me | S | CH | (5-aminomethylthiophen-2-yl) |
| 45 | CH₃CH(OH)— | Me | S | CH | (furan-2-yl) |
| 46 | CH₃CH(OH)— | Me | S | CH | (2-methylisoquinolinium-6-yl) |
| 47 | CH₃CH(OH)— | Me | S | CH | —C(O)NH₂ |
| 48 | CH₃CH(OH)— | Me | S | CH | —C(O)NMe₂ |
| 49 | CH₃CH(OH)— | Me | S | CH | —C(O)N(CH₂CH₂)₂N⁺Me₂ |
| 50 | CH₃CH(OH)— | Me | S | CH | —CH₂CH₂NH₂ |
| 51 | CH₃CH(OH)— | Me | S | CH | —CH₂CH₂CH₂NH₂ |
| 52 | CH₃CH(OH)— | Me | S | CH | —CH₂CH₂CH₂NMe₂ |
| 53 | CH₃CH(OH)— | Me | S | CH | —CH₂CH₂CH₂N⁺Me₃ |
| 54 | CH₃CH(OH)— | Me | S | CH | —CH₂CH₂OH |
| 55 | CH₃CH(OH)— | Me | S | CH | —CH₂CH₂CH₂OH |
| 56 | CH₃CH(OH)— | Me | S | N | (4-aminomethylphenyl) |
| 57 | CH₃CH(OH)— | Me | S | N | (3-aminomethylphenyl) |

TABLE 1-continued

| Comp. No. | R¹ | R² | X | Y¹ | Z |
|---|---|---|---|---|---|
| 58 | $CH_3CH(OH)-$ | Me | S | N | 4-(N-Me)-pyridinium |
| 59 | $CH_3CH(OH)-$ | Me | S | N | 4-(N-CH₂CONH₂)-pyridinium |
| 60 | $CH_3CH(OH)-$ | Me | S | N | 3-(N-Me)-pyridinium |
| 61 | $CH_3CH(OH)-$ | H | S | CH | 4-$CH_2NH_2$-phenyl |
| 62 | $CH_3CH(OH)-$ | H | S | CH | 3-$CH_2NH_2$-phenyl |
| 63 | $CH_3CH(OH)-$ | H | S | CH | 4-(N-Me)-pyridinium |
| 64 | $CH_3CH(OH)-$ | H | S | CH | 4-(N-CH₂CONH₂)-pyridinium |
| 65 | $CH_3CH(OH)-$ | H | S | CH | 3-(N-Me)-pyridinium |
| 66 | $HOCH_2-$ | Me | S | CH | 4-$CH_2NH_2$-phenyl |
| 67 | $HOCH_2-$ | Me | S | CH | 3-$CH_2NH_2$-phenyl |
| 68 | $HOCH_2-$ | Me | S | CH | 4-(N-Me)-pyridinium |
| 69 | $HOCH_2-$ | Me | S | CH | 4-(N-CH₂CONH₂)-pyridinium |

TABLE 1-continued

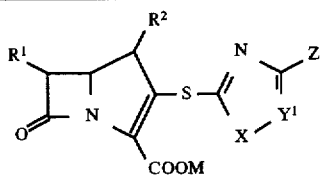

| Comp. No. | R¹ | R² | X | Y¹ | Z |
|---|---|---|---|---|---|
| 70 | CH₃CH(OH)— | Me | S | CH | 3-methyl-N-methylpyridinium |
| 71 | CH₃CH(OH)— | Me | S | CH | 4-(1-propenyl)-N-methylpyridinium |
| 72 | CH₃CH(OH)— | Me | S | CH | 4-(1-propenyl)-N-CH₂CONH₂-pyridinium |
| 73 | CH₃CH(OH)— | Me | S | CH | 4-(1-propenyl)-N-CH₂CONMe₂-pyridinium |
| 74 | CH₃CH(OH)— | Me | S | CH | 4-(1-propenyl, Z)-N-methylpyridinium |
| 75 | CH₃CH(OH)— | Me | S | CH | 4-(1-propenyl, Z)-N-CH₂CONH₂-pyridinium |
| 76 | CH₃CH(OH)— | Me | S | CH | 4-(1-propenyl, Z)-N-CH₂CONMe₂-pyridinium |
| 77 | CH₃CH(OH)— | Me | S | CH | 3-(1-propenyl)-N-methylpyridinium |
| 78 | CH₃CH(OH)— | Me | S | CH | 3-(1-propenyl)-N-CH₂CONH₂-pyridinium |
| 79 | CH₃CH(OH)— | Me | S | CH | 3-(1-propenyl)-N-CH₂CONMe₂-pyridinium |
| 80 | CH₃CH(OH)— | Me | S | CH | 3-(1-propenyl, Z)-N-methylpyridinium |
| 81 | CH₃CH(OH)— | Me | S | CH | 3-(1-propenyl, Z)-N-CH₂CONH₂-pyridinium |

TABLE 1-continued
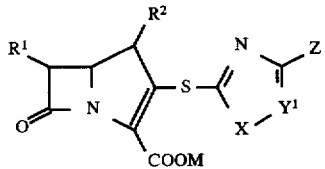
| Comp. No. | R¹ | R² | X | Y¹ | Z |
|---|---|---|---|---|---|
| 82 | CH$_3$CH(OH)— | Me | S | CH | 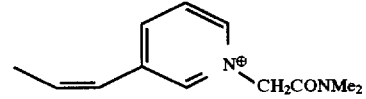 |
| 83 | CH$_3$CH(OH)— | Me | S | CH | 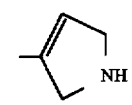 |
| 84 | CH$_3$CH(OH)— | Me | S | CH | 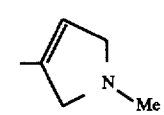 |
| 85 | CH$_3$CH(OH)— | Me | S | CH | 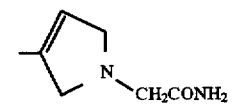 |
| 86 | CH$_3$CH(OH)— | Me | S | CH | 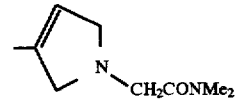 |
| 87 | CH$_3$CH(OH)— | Me | S | CH | 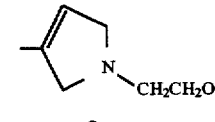 |
| 88 | CH$_3$CH(OH)— | Me | S | CH | 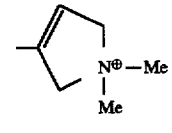 |
| 89 | CH$_3$CH(OH)— | Me | S | CH | 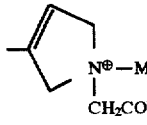 |
| 90 | CH$_3$CH(OH)— | Me | S | CH | 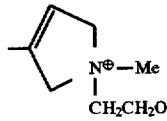 |
| 91 | CH$_3$CH(OH)— | Me | S | CH | 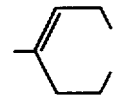 |
| 92 | CH$_3$CH(OH)— | Me | S | CH | 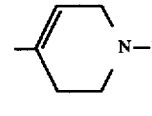 |
| 93 | CH$_3$CH(OH)— | Me | S | CH | 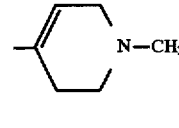 |

TABLE 1-continued

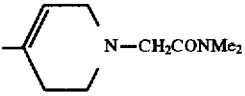

| Comp. No. | R¹ | R² | X | Y¹ | Z |
|---|---|---|---|---|---|
| 94 | CH₃CH(OH)— | Me | S | CH | 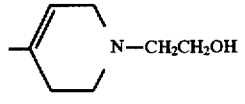 N—CH₂CONMe₂ |
| 95 | CH₃CH(OH)— | Me | S | CH | N—CH₂CH₂OH |
| 96 | CH₃CH(OH)— | Me | S | CH | N⊕(Me)(Me) |
| 97 | CH₃CH(OH)— | Me | S | CH | N⊕(Me)(CH₂CONH₂) |
| 98 | CH₃CH(OH)— | Me | S | CH | N⊕(Me)(CH₂CONH₂) |

The compounds exemplified in Table 1 have a stereoisomer, and these compounds also include stereoisomers thereof. Besides, M means a hydrogen atom except that when Z in Table 1 includes a cation, M means an anion.

Some of the novel β-lactam compounds of the formula [1] of the present invention show an excellent antibacterial activity against a wide variety of bacteria including gram-positive bacteria such as *Staphylococcus aureus, Staphylococcus epidermidis, Streptococcus pyogenes, Streptococcus pneumoniae, Enterococcus faecalis*, etc., and gram-negative bacteria such as *Escherichia coli*, Proteus bacteria, *Klebsiella pneumoniae, Haemophilus influenzae*, gonococcus, branhamella bacteria, but particularly, the compounds of the present invention characteristically show a potent antibacterial activity against gram-positive bacteria, especially against MRSA and MRCNS.

Dehydropeptidase-I (DHP-I), which is a renal enzyme, has been known to hydrolyze easily natural carbapenem compounds. However, some of the compounds of the formula [1] of the present invention, which are also carbapenem compounds, are stable to DHP-I and can be used alone, but if necessary, they can be used together with a DHP-I inhibitor.

When used as an antibacterial agent for treatment of infectious diseases caused by bacteria, the compounds of the present invention can be administered orally in the form of tablets, capsules, powders, syrups, etc., or administered parenterally by intravenous injection, intramuscular injection, or rectally.

The above-mentioned suitable preparations may be prepared by mixing an active ingredient with a conventional carrier, filler, binder, stabilizer, etc. When used in an injection form, the preparation may contain a pharmaceutically acceptable buffer, solubilizer, isotonic agent, etc.

The dosage of the present compound varies according to the conditions of diseases to be cured, ages and weights of patients, administration route, or frequency of administration, but it is usually in the range of 100 to 3000 mg per day for an adult, in a single administration unit or in several administration units. If necessary, the dosage of the present compounds may be increased or reduced.

BEST MODE OF CARRY OUT THE INVENTION

The present invention will be illustrated in more detail by Examples, but the present invention should not be construed to be limited thereto.

The following abbreviations are used in the following Examples.

PNB: p-Nitrobenzyl group
Ph: Phenyl group
TMS: Trimethylsilyl group  Me: Methyl group
Tf: Trifluoromethanesulfonyl group

EXAMPLE 1

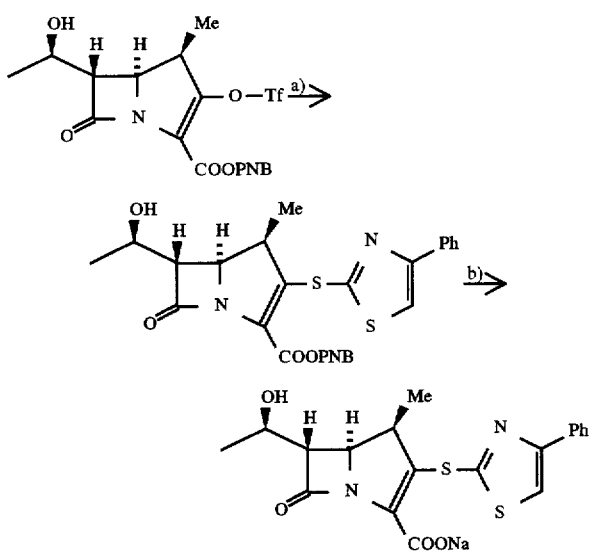

a) A solution of (4R,5R,6S,8R)-p-nitrobenzyl-3-trifluoromethanesulfonyloxy-4-methyl-6-(1-hydroxyethyl)-1-azabicyclo[3.2.0]hept-2-en-7-one-2carboxylate (1.0 mmol) in THF (3.0 ml) is stirred at −78° C., and thereto is added dropwise a thiolate salt solution, which is prepared by adding 2-mercapto-4-phenylthiazole (207 mg, 1.0 mmol) to a suspension of 60% sodium hydride (41 mg, 1.0 mmol) in THF (1.5 ml). The mixture is warmed to 0° C. over a period of four hours, and then stirred at the same temperature for one hour. The reaction solution is diluted with ethyl acetate, washed successively with a 2.5% aqueous potassium dihydrogen phosphate solution and a saturated sodium chloride solution, dried over magnesium sulfate, and evaporated to remove the solvent. The residue is purified by silica gel column chromatography (benzene/ethyl acetate=5~3) to give (4R,5S,6S,8R)-p-nitrobenzyl-3-(4phenylthiazole-hydroxyethyl)-1-azabicyclo[3.2.0]hepto-2-en-7-one-2-carboxylate (361 mg, yield; 67%) as pale yellow crystals.

IR$_{max}$ cm$^{-1}$ (neat): 3542, 1774, 1734, 1522, 1347

$^1$H-NMR δ (CDCL$_3$): 1.14 (3H, d, J=7.3 Hz), 1.33 (3H, d, J=6.3 Hz), 3.30 (1H, dd, J=2.6 Hz and 6.6 Hz), 3.66 (1H, m), 4.30 (2H, m), 5.30 (1H, d, J=13.9 Hz) 539 (1H, d, J=13.9 Hz), 7.44 (3H, m, 7.68 (2H, d, J=8.9 Hz) 7.89 (2H, d, J=6.9 Hz), 8.25 (2H, d, J=8.9 Hz)

b) 4R,5S,6S,8R)-p-Nitrobenzyl-3-(4-phenylthiazol-2-ylthio)-4-methyl-6-(1-hydroxyethyl) -1-azabicyclo[3.2.0] hepto-2-en-2-carboxylate (650 mg, 1.21 mmol) is dissolved in THF (35 ml) and a 0.05M sodium 4-morpholinopropanesulfonate buffer (pH 7.0, 35 ml), and thereto is added 10% palladiumcarbon (650 mg). The mixture is subjected to hydrogenation at a room temperature under atmospheric pressure for one hour. The catalyst is removed by filtration, and the filtrate is washed three times with dichloromethane. The aqueous layer is evaporated to remove the solvent, and the residue is purified by polymer chromatography (CHP-20P), and the fractions eluted with aqueous 8–16% THF solution are combined and lyophilized to give sodium (4R,5S,6S,8R)-3-(4-phenylthiazol-2-ylthio)-4-methyl-6-(1-hydroxyethyl)-1-azabicyclo[3.2.0]hept-2-en-7one-2-carboxylate as white amorphous.

UV$_{max}$ nm (H$_2$O): 320 (sh), 290, 247, 225 (sh)
IR$_{max}$ cm$^{-1}$ (KBr): 3495, 1734, 1477, 1369

$^1$H-NMR δ (D$_2$O) 1.11 (3H, d, J=7.3 Hz), 1.27 (3H, d, J=6.6 Hz), 3.60 (2H, m), 4.27 (1H, m), 4.37 (1H, dd, J=2.6 Hz and 9.6 Hz), 7.46 (3H, m), 7.70 (3H, s)

EXAMPLE 2

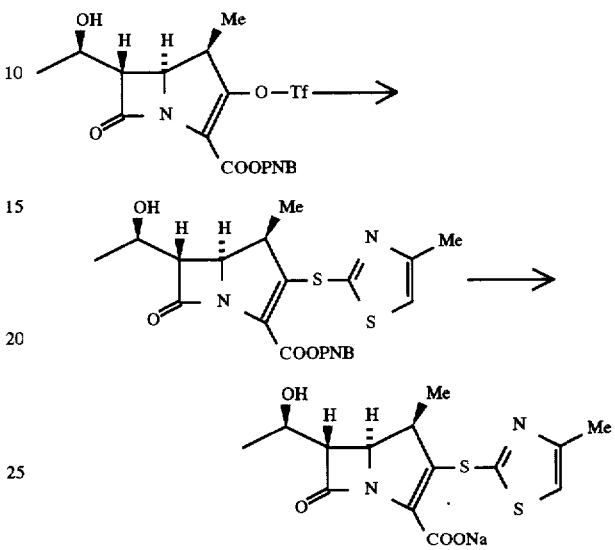

In the same manner as in Example 1 except that 2-mercapto-4-methylthiazole is used, there is obtained sodium (4R,5S,6S,8R)-3-(4-methylthiazol2-ylthio)-4-methyl-6(1-hydroxyethyl)-1-azabicyclo[3.2.0]hept-2-en-7-one-2carboxylate via (4R,5S,6S,8R)-p-nitrobenzyl-3-(4-methylthiazol-2-ylthio)-4methyl-6-(1-hydroxyethyl)-1-azabicyclo[3.2.0]hept-2-en-7-one-2-carboxylate.

(4R,5S,6S,8R)-p-Nitrobenzyl-3-(4-methylthiazol-2-ylthio)-4-methyl-6-(1hydroxyethyl)-1-azabicyclo[3.20] hept-2-en-7-one-2-carboxylate Pale yellow crystals IR$_{max}$ cm$^{-1}$ (KBr): 3449, 1809, 1705, 1527, 1327

$^1$H-NMR δ (CDCL$_3$): 1.09 (3H, d, J=7.3 Hz), 1.34 (3H, d, J=6.3 Hz), 2.48 (3H, d, J=1.0 Hz), 3.28 (1H, dd, J=2.6 Hz and 6.6 Hz), 3.50 (1H, m), 4.28 (2H, m), 5.28 (1H, d, J=13.9 Hz), 5.52 (1H, d, J=13.9 Hz), 7.66 (2H, d, J=8.9 Hz), 8.23 (2H, d, J=8.9 Hz)

Sodium (4R,5S,6S,8R)-3-(4-methylthiazol-2-ylthio)-4-methyl-6-(1-hydroxyethyl)-1-azabicyclo[3.2.0]hept-2-en-7-one-2-carboxylate White amorphous UV$_{max}$ nm (H$_2$O): 309

IR$_{max}$ cm$^{-1}$ (KBr): 3422, 1753, 1604, 1396

$^1$H-NMR δ (D$_2$O): 1.07 (3H, d, J=7.3 Hz), 1.27 (3H, d, J=6.6 Hz), 2.43 (3H, d, J=1.0 Hz), 3.22 (1H, m), 3.47 (1H, dd, J=2.6 Hz and 5.9 Hz), 4.23 (2H, m), 7.29 (1H, q, J=1.0 Hz)

EXAMPLE 3

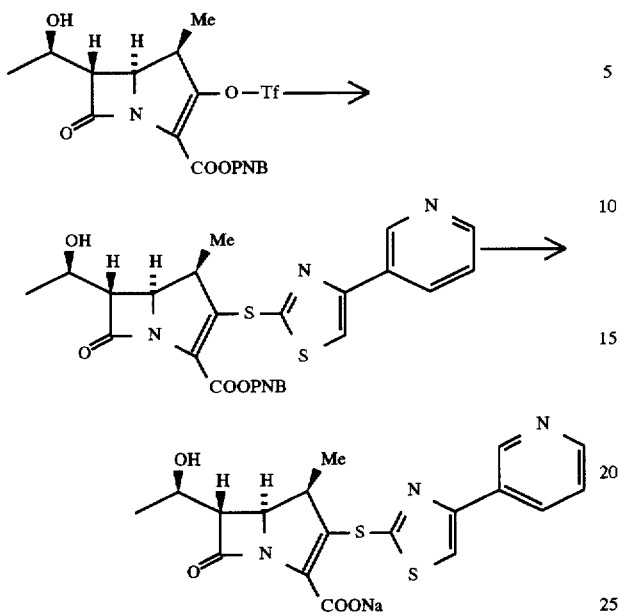

In the same manner as in Example 1 except that 2-mercapto-4-(3-pyridyl)thiazole is used, there is obtained sodium (4R,5S,6S,8R)-3-pyridyl)thiazol-2-ylthio)-4-methyl-6-(1-azabicyclo[3.2.0]hept-2-en-7-one-2-carboxylate via (4R,5S,6S,8R)-p-nitrobenzyl-3-(4-(3-pyridyl)thiazol-2-ylthio)-4-methyl-6-(1-hydroxyethyl)-1-azabicyclo[3.2.0]hept-2-en-7-one-2-carboxylate.

(4R,5S,6S,8R)-p-Nitrobenzyl-3-(4-(3-pyridyl)thiazol-2-ylthio)-4-methyl-6-(1-hydroxyethyl)-1-azabicyclo[3.2.0] hept-2-en-7-one-2-carboxylate Pale yellow oil IR$_{max}$ cm$^{-1}$ (neat): 3539, 1772, 1700, 1522, 1345

$^1$H-NMR δ (CDCL$_3$): 1.15 (3H, d, J=7.3 Hz), 1.33 (3H, d, J=6.3 Hz), 3.31 (1H, dd, J=2.6 Hz and 6.6 Hz), 3.67 (1H, m), 4.26 (1H, m), 4.32 (1H, dd, J=2.6 Hz and 9.6 Hz), 5.30 (1H, d, J=13.9 Hz), 5.55 (1H, d, J=13.9 Hz), 7.38 (1H, ddd, J=0.7 Hz, 5.0 Hz and 7.9 Hz), 7.78 (1H, s), 7.68 (2H, d, J=8.6 Hz), 8.19 (1H, td, J=2.0 Hz and 7.9 Hz), 8.24 (2H, d, J=8.6 Hz), 8.61 (1H, dd, J=2.0 Hz and 5.0 Hz), 9.12 (1H, dd, J=0.7 Hz and 2.0 Hz)

Sodium (4R,5S,6S,8R)-3-(4-(3-pyridyl)thiazol-2-ylthio)-4-methyl-6-(1-hydroxyethyl)-1-azabicyclo[3.2.0]hept-2-en-7-one-2-carboxylate Pale yellow amorphous UV$_{max}$ nm (H$_2$O): 315 (sh), 280, 221 (sh)

IR$_{max}$ cm$^{-1}$ (KBr): 3422, 1752, 1604, 1395

$^1$H-NMR δ (D$_2$O): 1.10 (3H, d, J=7.3 Hz), 1.26 (3H, d, J=6.6 Hz), 3.36 (1H, m), 3.49 (1H, dd, J=3.3 Hz and 5.9 Hz), 4.26 (2H, m), 7.70 (1H, dd, J=5.0 Hz and 6.9 Hz), 8.06 (1H, s), 8.40 (1H, d, J=6.9 Hz), 8.58 (1H, d, J=5.0 Hz), 8.98 (1H, s)

EXAMPLE 4

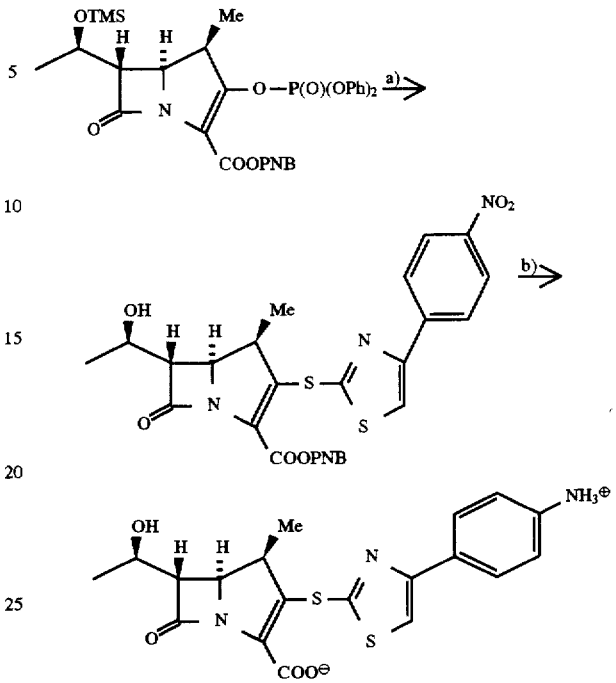

a) A solution of (4R,5R,6S,8R)-p-nitrobenzyl-3-(diphenylphosphoryloxy)-4-methyl-6-(1-(trimethylsilyloxy)ethyl)-1-azabicyclo[3.2.0]hept-2-en-7-one-2-carboxylate (1.33 g, 2.0 mmol) in toluene (2.0 ml) is stirred at 0° C. while thereto is gradually added a suspension of a thiolate salt which is prepared by adding 2-mercapto-4-(4-nitrophenyl)thiazole (619 mg, 2.6 mmol) into a suspension of sodium hydride (104 mg, 2.6 mmol) in THF (5.0 ml). The mixture is allowed to stand at 5° C. for 18 hours. The resulting reaction mixture is diluted with ethyl acetate, washed twice with water, and further washed with a saturated sodium chloride solution. The mixture is dried over magnesium sulfate, evaporated to remove the solvent, and the resulting brown solid is dissolved in ethyl acetate (100 ml). To the mixture is added 1N hydrochloric acid (3.0 ml, 3.0 mmol) under ice-cooling, and stirred for 30 minutes after being removed from an ice bath. The reaction solution is washed twice with water, washed once with a saturated sodium chloride solution, dried over magnesium sulfate, evaporated to remove the solvent. The residue is crystallized from benzene to give (4R,5S,6S,8R)-p-nitrobenzyl-3-(4-(4-nitrophenyl)thiazol-2-ylthio)-4-methyl-6-(1-hydroxyethyl)-1-azabicyclo[3.2.0]hept-2-en-7-one-2carboxylate (454 mg, yield; 39%) as pale brown crystals.

IR$_{max}$ cm$^{-1}$ (KBr): 3448, 1778, 1702, 1510, 1344

1H-NMR δ (CDCL$_3$): 1.16 (3H, d, J=7.3 Hz), 1.34 (3H, d, J=6.3 Hz), 3.32 (1H, dd, J=3.0 Hz and 6.6 Hz), 3.64 (1H, m), 4.26 (1H, m), 4.34 (1H, dd, J=3.0 Hz and 9.9 Hz), 5.30 (1H, d, J=13.9 Hz), 5.56 (1H, d, J=13.9 Hz), 7.68 (2H, d, J=8.9 Hz), 7.78 (1H, s), 8.06 (2H, d, J=8.9 Hz), 8.24 (2H, d, J=8.9 Hz), 8.31 (2H, d, J=8.9 Hz)

b) In the same deprotection reaction as in Example 1, (4R,5S,6S,8R)-3-(4-(4-ammoniumphenyl)thiazol-2-ylthio)-4-methyl-6-(1-hydroxyethyl)-1-azabicyclo[3.2.0] hept-2-en-7-one-2-carboxylate is obtained as yellow amorphous from (4R,5S,6S,8R)-p-nitrobenzyl-3-(4-(4-nitrophenyl)thiazol-2-ylthio)-4-methyl-6-(1-hydroxyethyl)-1-azabicyclo[3.2.0]hept-2-en-7-one-2-carboxylate.

UV$_{max}$ nm (H$_2$O): 285

IR$_{max}$ cm$^{-1}$ (KBr): 3347, 1762, 1602, 1476, 1394

$^1$H-NMR δ (D$_2$O): 1.01 (3H, d, J=7.3 Hz), 1.23 (3H, d, J=6.6 Hz), 3.21 (1H, m), 3.43 (1H, dd, J=3.0 Hz and 5.9 Hz), 4.20 (2H, m), 7.10 (2H, d, J=8.36 Hz), 7.65 (1H, s), 7.69 (2H, d, J=8.6 Hz)

EXAMPLE 5

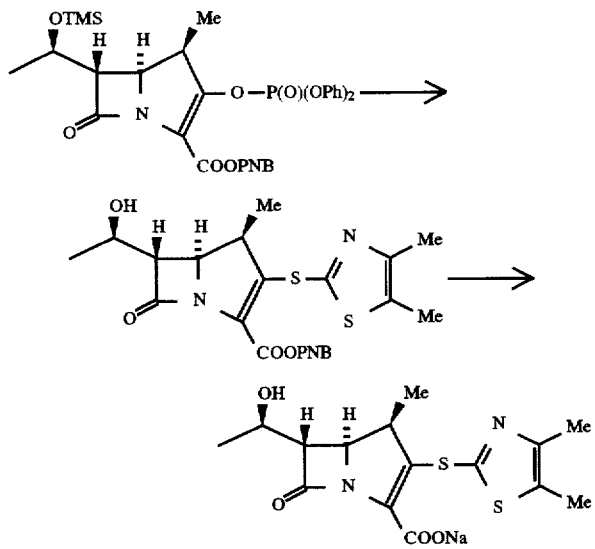

In the same manner as in Example 4 except that 2-mercapto-4,5-dimethylthiazole is used, sodium (4R,5S,6S,8R)-3-(4,5-dimethylthiazol-2-ylthio)-4-methyl-6-(1-hydroxyethyl)-1-azabicyclo[3.2.0]hept-2-en-7-one-2-carboxylate is obtained via (4R,5S,6S,8R)-p-nitrobenzyl-3-(4,5-dimethylthiazol-2-ylthio)-4methyl-6-(1-hydroxyethyl)-1-azabicyclo[3.2.0]hept-2-en-7one-2-carboxylate.

(4R,5S,6S,8R)-p-Nitrobenzyl-3-(4,5-dimethylthiazol-2-ylthio)-4-methyl-6-(1hydroxyethyl)-1-azabicyclo[3.2.0]hept-2-en-7-one-2-carboxylate White crystals IR$_{max}$ cm$^{-1}$ (KBr): 3567, 1771, 1701, 1518, 1346

$^1$H-NMR δ (CDCL$_3$): 1.11 (3H, d, J=7.3 Hz), 1.34 (3H, d, J=6.3 Hz), 2.36 (3H, s), 2.37 (3H, s), 3.27 (1H, dd, J=2.6 Hz and 6.6 Hz), 3.44 (1H, m), 4.25 (2H, m), 5.28 (1H, d, J=13.9 Hz), 5.52 (1H, d, J=13.9 Hz), 7.66 (2H, d, J=8.9 Hz), 8.23 (2H, d, J=8.9 Hz)

Sodium (4R,5S,6S,8R)-3-(4,5-dimethylthiazol-2-ylthio)-4-methyl-6-(1-hydroxyethyl)-1-azabicyclo[3.2.0]hept-2-en-7-one-2-carboxylate White amorphous UV$_{max}$ nm (H$_2$O): 310

IR$_{max}$ cm$^{-1}$ (KBr): 3408, 1765, 1376

$^1$H-NMR δ (D$_2$O): 1.07 (3H, d, J=7.3 Hz), 1.27 (3H, d, J=6.6Hz), 2.31 (3H, s), 2.38 (3H, s), 3.18 (1H, m), 3.43 (1H, dd, J=3.0 Hz and 5.9 Hz), 4.26 (2H, m)

EXAMPLE 6

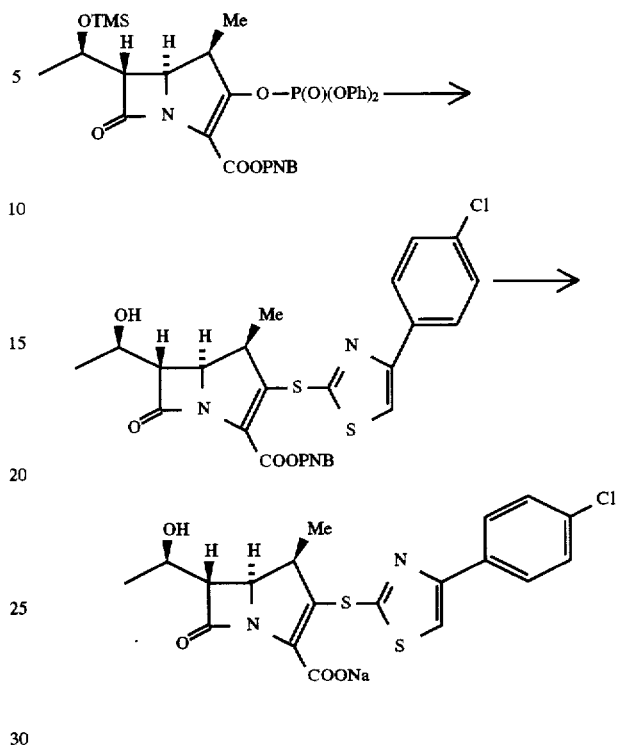

In the same manner as in Example 4 except that 2-mercapto-4-(4-chlorophenyl)thiazole is used, sodium (4R,5S,6S,8R)-3-(4-(4-chlorophenyl)thiazol-2-ylthio)-4-methyl-6-(1-hydroxyethyl)-1-azabicyclo[3.2.0]hept-2-en-7one-2carboxylate is obtained via (4R,5S,6S,8R)-p-nitrobenzyl-3-(4-(4-chlorophenyl)thiazol-2-ylthio)-4-methyl-6-(1-hydroxyethyl)-1-azabicyclo[3.2.0]hept2-en-7-one-2-carboxylate.

(4R,5S,6S,8R)-p-Nitrobenzyl-3-(4-(4-chlorophenyl)thiazol-2-ylthio)-4-methyl-6-(1-hydroxyethyl)-1-azabicyclo[3.2.0]hept-2-en-7-one-2-carboxylate Colorless oil IR$_{max}$ cm$^{-1}$ (neat): 3567, 1771, 1701, 1518, 1346

$^1$H-NMR δ (CDCL$_3$): 1.13 (3H, d, J=7.3 Hz), 1.32 (3H, d, J=6.3 Hz), 3.29 (1H, dd, J=3.0 Hz and 6.6 Hz), 3.61 (1H, m), 4.30 (2H, m), 5.29 (1H, d, J=13.5 Hz), 5.53 (1H, d, J=13.5 Hz), 7.41 (2H, d, J=8.6 Hz), 7.55 (1H, s), 7.67 (2H, d, J=8.6 Hz), 7.81 (2H, d, J=8.6 Hz), 8.22 (2H, d, J=8.6 Hz)

Sodium (4R,5S,6S,8R)-3-(4-(4-chlorophenyl)thiazol-2-ylthio)-4-methyl6-(1-hydroxyethyl)-1-azabicyclo[3.2.0]hept-2-en-7-one-2-carboxylate White amorphous UV$_{max}$ nm (H$_2$O): 310 (sh), 266

IR$_{max}$ cm$^{-1}$ (KBr): 3428, 1758, 1603, 1395

$^1$H-NMR δ (D$_2$O): 1.09 (3H, d, J=7.3 Hz), 1.25 (3H, d, J=6.3 Hz), 3.31 (1H, m), 3.46 (1H, dd, J=3.0 Hz and 5.9 Hz), 4.25 (2H, m), 7.48 (2H, d, J=8.6 Hz), 7.77 (2H, J=8.6 Hz), 7.87 (1H, s)

EXAMPLE 7

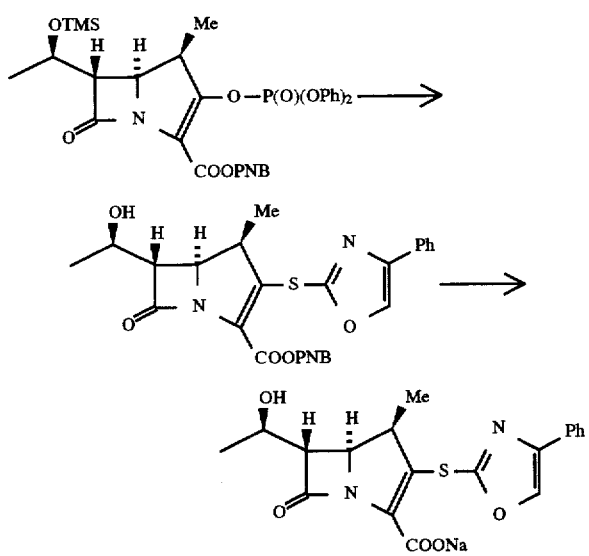

In the same manner as in Example 4 except that 2-mercapto-4-phenyloxazole is used, sodium (4R,5S,6S,8R)-3-(4-phenyloxazol-2-ylthio)-4-methyl-6-(1-hydroxyethyl)-1-azabicyclo[3.2.0]hept-2-en-7-one-2-carboxylate is obtained via (4R,5S,6S,8R)-p-nitrobenzyl-3-(4-phenyloxazol-2-ylthio)-4methyl-6-(1-hydroxyethyl)-1-azabicyclo[3.2.0]hept-2-en-7-one-2-carboxylate. (4R,5S,6S,8R)-p-Nitrobenzyl-3-(4-phenyloxazol-2-ylthio)-4-methyl-6-(1-hydroxyethyl)-1-azabicyclo[3.2.0]hept-2-en-7-one-2-carboxylate Pale brown crystals $IR_{max}$ cm$^{-1}$ (KBr): 3406, 1760, 1696, 1518, 1344

$^1$H-NMR δ (CDCL$_3$): 1.13 (3H, d, J=7.3 Hz), 1.33 (3H, d, J=6.3 Hz), 3.32 (1H, dd, J=3.0 Hz and 6.6 Hz), 3.63 (1H, m), 4.26 (1H, m), 4.34 (1H, dd, J=3.0 Hz and 9.9 Hz), 5.30 (1H, d, J=13.5 Hz), 5.52 (1H, d, J=13.5 Hz), 7.40 (5H, m), 7.66 (2H, d, J=8.6 Hz), 7.72 (2H, d, J=8.6 Hz), 8.03 (1H, s), 8.23 (2H, J=8.6 Hz)

Sodium (4R,5S,6S,8R)-3-(4-phenyloxazol-2-ylthio)-4-methyl-6-(1-hydroxyethyl)-1-azabicyclo[3.2.0]hept-2-en-7-one-2-carboxylate White amorphous UV$_{max}$ nm (H$_2$O): 299, 248

$IR_{max}$ cm$^{-1}$ (KBr): 3424, 1758, 1603, 1397

$^1$H-NMR δ (D$_2$O): 1.09 (3H, d, J=7.3 Hz), 1.27 (3H, d, J=6.3 Hz), 3.27 (1H, m), 3.46 (1H, dd, J=2.6 Hz and 5.9 Hz), 4.28 (2H, m), 7.62 (3H, m), 7.74 (2H, J=6.9 Hz), 8.38 (1H, s)

EXAMPLE 8

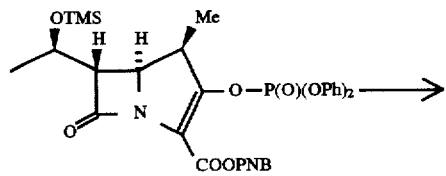

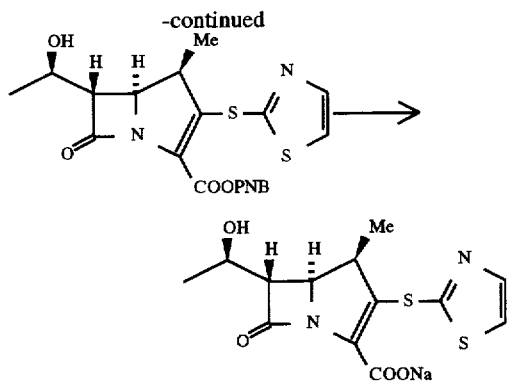

In the same manner as in Example 4 except that 2-mercaptothiazole is used, sodium (4R,5S,6S,8R)-3-(thiazol-2-ylthio)-4-methyl-6-(1-hydroxyethyl)-1-azabicyclo[3.2.0]hept-2-en-7-one-2-carboxylate is obtained via (4R,5S,6S,8R)-p-nitrobenzyl-3-(thiazol-2-ylthio)-4-methyl-6-(1-hydroxyethyl)-1-azabicyclo[3.2.0]hept-2-en-7-one-2-carboxylate. (4R,5S,6S,8R)-p-Nitrobenzyl-3-(thiazol-2-ylthio)-4-methyl-6-(1-hydroxyethyl)-1-azabicyclo[3.2.0]hept-2-en-7-one-2-carboxylate Pale yellow oil $IR_{max}$ cm$^{-1}$ (neat): 3406, 1760, 1696, 1518, 1344

$^1$H-NMR δ (CDCL$_3$): 1.04 (3H, d, J=7.3 Hz), 1.28 (3H, d, J=6.6 Hz), 3.26 (1H, dd, J=3.0 Hz and 6.6 Hz), 3.46 (1H, m), 4.26 (2H, m), 5.26 (1H, d, J=13.9 Hz), 5.50 (1H, d, J=13.9 Hz), 7.47 (1H, d, J=3.3 Hz), 7.64 (2H, d, J=8.6 Hz), 7.85 (2H, d, J=3.3 Hz), 8.19 (2H, d, J=8.6 Hz)

Sodium (4R,5S,6S,8R)-3-(thiazol-2-ylthio)-4-methyl-6-(1-hydroxyethyl)-1-azabicyclo[3.2.0]hept-2-en-7-one-2-carboxylate White amorphous UV$_{max}$ nm (aq. 2 % NaHCO$_3$): 308

$IR_{max}$ cm$^{-1}$ (KBr): 3372, 1767, 1706, 1207

$^1$H-NMR δ (D$_2$O): 1.07 (3H, d, J=7.3 Hz), 1.26 (3H, d, J=6.3 Hz), 3.20 (1H, m), 3.47 (1H, dd, J=2.6 Hz and 5.9 Hz), 4.24 (2H, m), 7.74 (1H, d, J=3.3 Hz), 7.88 (1H, d, J=3.3 Hz)

EXAMPLE 9

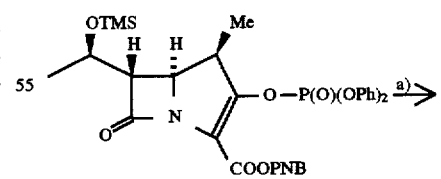

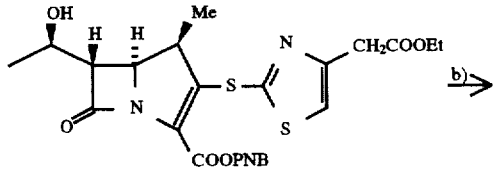

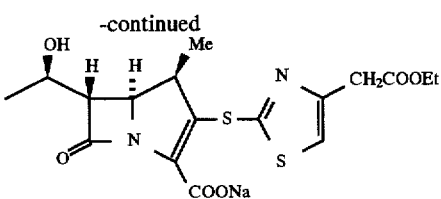

a) A solution of (4R,5R,6S,8R)-p-nitrobenzyl-3-(diphenylphosphoryloxy)4-methyl-6-(1-(trimethylsilyloxy)ethyl)-1-azabicyclo[3.2.0]hept-2-en-7-one-2carboxylate (1.34 g, 2.0 mmol) in toluene (2.0 ml) is stirred at 0° C., while thereto are added dimethylformamide (3.0 ml), 2-mercapto-4-ethoxycarbonylmethylthiazole (447 mg, 2.2 mmol) and DBU (420 mg, 2.6 mmol), and the mixture is allowed to stand at 5° C. for four days. The resulting reaction mixture is diluted with ethyl acetate, washed twice with water and washed once with a saturated sodium chloride solution, dried over magnesium sulfate, and evaporated to remove the solvent. The resulting black oily product is dissolved again in ethyl acetate (80 ml), and thereto is added 1 N hydrochloric acid (3.0 ml, 3.0 mmol) under ice-cooling. The mixture is stirred for 30 minutes after being removed from an ice bath. The reaction solution is washed twice with water, and washed once with a saturated sodium chloride solution, dried over magnesium sulfate, and evaporated to remove the solvent. The residue is purified by silica gel column chromatography (benzene/ethyl acetate=2) to give (4R,5S,6S,8R)-p-nitrobenzyl-3-(4-ethoxycarbonylmethylthiazol-2-ylthio)-4-methyl-6-hydroxyethyl)-1-azabicyclo[3.2.0]hept-2-en-7-one-2-carboxylate as pale yellow oil (yield; 46%).

IR max cm$^{-1}$ (neat): 3502, 1762, 1734, 1521

$^1$H-NMR δ (CDCL$_3$): 1.06 (3H, d, J=7.3 Hz), 1.32 (6H, m), 3.27 (1H, dd, J=3.0 Hz and 6.6 Hz), 3.49 (1H, m), 3.85 (2H, s), 4.25 (4H, m), 5.27 (1H, d, J=13.9 Hz), 5.50 (1H, d, J=13.9 Hz), 7.33 (1H, s), 7.65 (2H, d, J=8.9 Hz), 8.21 (2H, d, J=8.9 Hz)

b) In the same deprotection procedure as in Example 1, sodium (4R,5S,6S,8R)-3-(4-ethoxycarbonylmethylthiazol-2-ylthio)-4-methyl-6-(1-hydroxyethyl)-1-azabicyclo[3.2.0]hept-2en-7-one-2-carboxylate is obtained as white amorphous from (4R,5S,6S,8R)-p-nitrobenzyl-3-(4-ethoxycarbonylmethylthiazol-2-ylthio)-4-methyl-6-(1-hydroxyethyl)-1-azabicyclo[3.2.0]hept-2en-7-one-2-carboxylate.

UV$_{max}$ nm (H$_2$O): 313, 269 (sh)
IR$_{max}$ cm$^{-1}$ (KBr): 3388, 1734, 1605, 1394

$^1$H-NMR δ (D$_2$O): 1.07 (3H, d, J=7.3 Hz), 1.27 (6H, m), 3.24 (1H, m), 3.47 (1H, dd, J=2.6 Hz and 5.9 Hz), 3.94 (2H, s), 4.24 (4H, m), 7.56 (1H, s)

EXAMPLE 10

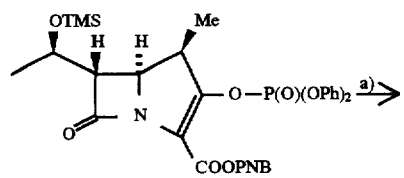

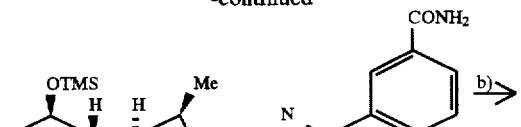

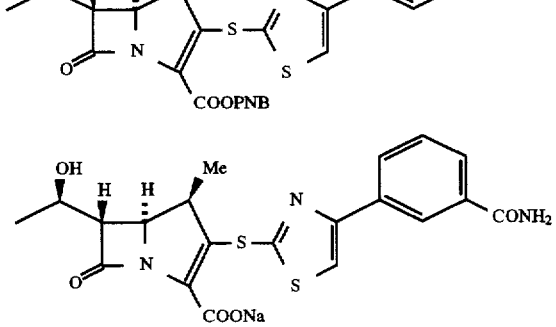

a) A solution of (4R,5R,6S,8R)-p-nitrobenzyl-3-(diphenylphosphoryloxy)-4-methyl-6-(1-(trimethylsilyloxy)ethyl)-1-azabicyclo[3.2.0]hept-2-en-7-one-2-carboxylate (0.67 g, 1.0 mmol) in toluene (1.0 ml) is stirred at 0° C., while thereto is added a solution of a thiolate salt which is prepared by adding a solution of 2-mercapto-4-(3-aminocarbonylphenyl)-thiazole (354 mg, 1.5 mmol) in DMF (2.0 ml) into a solution of sodium hydride (60 mg, 1.5 mmol) in THF (2.0 ml). The mixture is allowed to stand at 5° C. for 18 hours. The reaction solution is diluted with ethyl acetate, washed twice with water and washed once with a saturated sodium chloride solution, dried over magnesium sulfate, and evaporated to remove the solvent. The residue is purified by silica gel column chromatography (benzene/ethyl acetate=2~1) to give (4R,5S,6S,8R)-p-nitrobenzyl-3-(4-(3-aminocarbonylphenyl)thiazol-2-ylthio)-4-methyl-6-(1-(trimethylsilyloxy)ethyl)-1-azabicyclo[3.2.0]hept-2-en-7one-2caroxylate (326 mg, yield; 50 %) as yellow oily product.

IR$_{max}$ cm$^{-1}$ (neat): 3362, 1772, 1684, 1522, 1340

$^1$H-NMR δ (CDCL$_3$): 0.10 (9H, s), 1.13 (3H, d, J=7.3 Hz), 1.20 (3H, d, J=5.9 Hz), 3.27 (1H, dd, J=3.0 Hz and 5.3 Hz), 3.54 (1H, m), 4.25 (2H, m), 5.31 (1H, d, J=13.9 Hz), 5.56 (1H, d, J=13.9 Hz), 5.65 (1H, br.), 6.23 (1H, br.), 7.53 (1H, t, J=7.6 Hz), 7.65 (2H, d, J=8.6 Hz), 7.67 (1H, s), 7.80 (1H, dd, J=1.3 Hz and 7.6 Hz), 8.05 (1H, dd, J=1.3 and 7.6 Hz), 8.23 (2H, d, J=8.6 Hz), 8.33 (1H, t, J=1.3 Hz)

b) In the same deprotection procedure as in Example 1, sodium (4R,5S,6S,8R)-3-(4-(3-aminocarbonylphenyl)thiazol-2-ylthio)-4-methyl-6-(1-hydroxyethyl)-1-azabicyclo[3.2.0]hept-2-en-7-one-2-carboxylate is obtained as white amorphous from (4R,5S,6S,8R)-p-nitrobenzyl-3-(4-(3-aminocarbonylphenyl)thiazol-2-ylthio)-4-methyl-6-(1-(trimethylsilyloxy)ethyl)-1-azabicyclo[3.2.0]hept-2-en-7-one-2-carboxylate.

UV$_{max}$ nm (H$_2$O): 318 (sh), 269 (sh), 215 (sh)
IR$_{max}$ cm$^{-1}$ (KBr): 3425, 1752, 1670, 1603, 1394

$^1$H-NMR δ (D$_2$O): 1.09 (3H, d, J=6.9 Hz), 1.26 (3H, d, J=6.6 Hz), 3.32 (1H, m), 3.47 (1H, dd, J=3.0 Hz and 5.9 Hz), 4.25 (2H, m), 7.60 (1H, dd, J=5.9 Hz and 7.9 Hz), 7.85 (1H, dd, J=0.7 Hz and 5.9 Hz), 7.90 (1H, s), 7.97 (1H, d, J=7.9 Hz), 8.16 (1H, d, J=0.7 Hz)

EXAMPLE 11

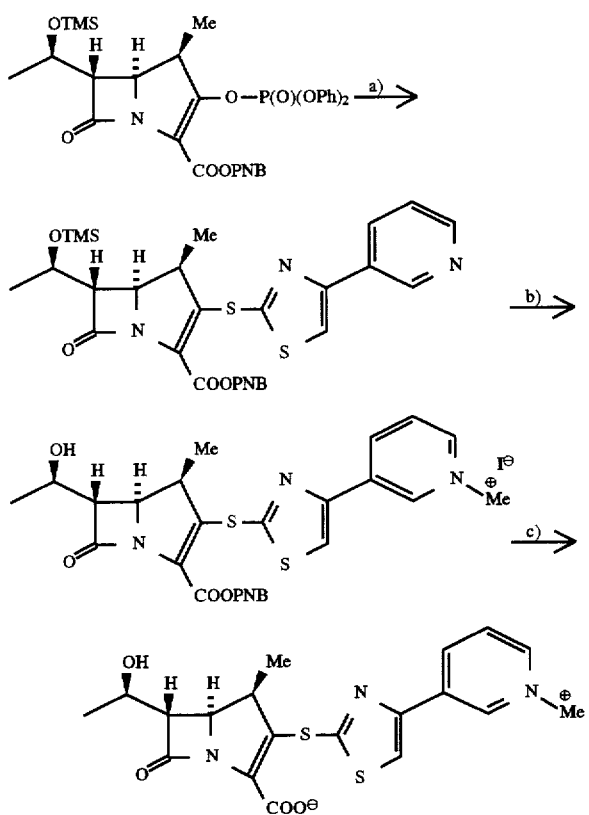

a) (4R,5S,6S,8R)-p-Nitrobenzyl-3-(4-(3-pyridyl)thiazol-2-ylthio)-4-methyl-6-(1-(trimethylsilyloxy)ethyl)-1-azabicyclo[3.2.0]hept-2-en-7-one-2-carboxylate is obtained as pale yellow crystals in the same manner as in Example 10 except that 2-mercapto-4-(3-pyridyl)thiazole is used (yield; 61%).

IR$_{max}$ cm$^{-1}$ (KBr): 1772, 1700, 1522, 1340

$^1$H-NMR δ (CDCL$_3$): 0.10 (9H, s), 1.13 (3H, d, J=7.3 Hz), 1.20 (3H, d, J=6.3 Hz), 3.28 (1H, dd, J=3.0 Hz and 5.6 Hz), 3.62 (1H, m), 4.26 (2H, m 5.30 (1H, d, J=13.9 Hz), 5.50 (1H, d, J=13.9 Hz), 7.38 (1H, ddd, J=0.7 Hz, 5.0 Hz and 7.9 Hz), 7.67 (1H, s), 7.67 (2H, d, J=8.9 Hz), 8.19 (1H, td, J=1.7 Hz and 7.9 Hz), 8.22 (2H, d, J=8.9 Hz), 8.60 (1H, dd, J=1.7 Hz and 5.0 Hz), 9.11 (1H, dd, J=0.7 Hz and 1.7 Hz)

b) To a solution of (4R,5S,6S,8R)-p-nitrobenzyl-3-(4-(3-pyridyl)thiazol-2-ylthio)-4-methyl-6-(1-trimethylsilyloxy)ethyl-1-azabicyclo[3.2.0]hept-2-en-7-one-2-carboxylate in acetone (10 ml) is added methyl iodide (1.0 ml), and the mixture is allowed to stand at room temperature for one day. The insoluble materials are collected by filtration, washed with acetone, and dried under reduced pressure to give (4R,5S,6S,8R)-p-nitrobenzyl-3-(4-(1-methylpyridinium-3-yl)thiazol-2-ylthio)-4-methyl-6-(1-(trimethylsilyloxy)ethyl)-1-azabicyclo[3.2.0]hept-2-en7-one-2-carboxylate iodide (339 mg, yield; 74 %).

IR$_{max}$ cm$^{-1}$ (KBr): 1782, 1522, 1341

$^1$H-NMR δ (DMSO d-6): 0.08 (9H, s), 1.03 (3H, d, J=7.3 Hz), 1.11 (3H, d, J=6.3 Hz), 3.60 (2H, m), 4.26 (1H, m), 4.37 (1H, dd, J=3.3 Hz and 10.6 Hz), 4.82 (3H, s), 5.41 (1H, d, J=14.2 Hz), 5.52 (1H, d, J=14.2 Hz), 7.74 (2H, d, J=8.9 Hz), 8.22 (3H, m), 8.75 (1H, s), 8.96 (1H, d, J=5.9 Hz), 9.06 (1H, d, J=8.6 Hz), 9.55 (1H, s)

c) In the same deprotection procedure as in Example 1, (4R,5S,6S,8R)-3-(4-(1-methylpyridinium-3-yl)thiazol-2-ylthiol)-4-methyl-6-(1-hydroxyethyl)-1-azabicyclo[3.2.0]hept-2-en-7-one-2-carboxylate is obtained as white amorphous from (4R,5S,6S,8R)-p-nitrobenzyl-3-(4-(1-methylpyridinium-3-yl)-thiazol -2-ylthio)-4-methyl-6-(1-(trimethylsilyloxy)ethyl)-1-azabicyclo[3.2.0]hept2-en-7-one-2-carboxylate iodide.

UV$_{max}$ nm (H$_2$O): 303, 264

IR$_{max}$ cm$^{-1}$ (KBr): 3424, 1762, 1602, 1388

$^1$H-NMR δ (D$_2$O): 1.10 (3H, d, J=7.3 Hz), 1.26 (3H, d, J=6.3 Hz), 3.39 (1H, m), 3.50 (1H, dd, J=3.0 Hz and 5.9 Hz), 4.26 (2H, m), 4.48 (3H, s), 8.12 (1H, dd, J=5.9 Hz and 8.3 Hz), 8.30 (1H, s), 8.77 (1H, d, J=5.9 Hz), 8.90 (1H, d, J=8.3 Hz), 9.29 (1H, s)

EXAMPLE 12

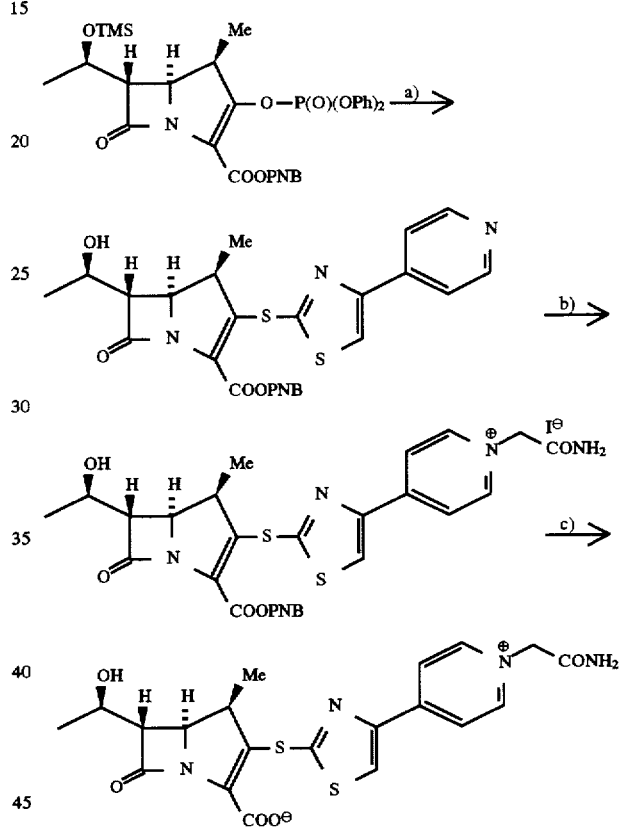

a) (4R,5S,6S,8R)-p-Nitrobenzyl-3-(4-(4-pyridyl)thiazol-2-ylthio)-4-methyl1 6-(1-hydroxyethyl)-1-azabicyclo [3.2.0]hept-2-en-7-one-2-carboxylate is obtained as pale yellow crystals in the same manner as in Example 4 except that 2-mercapto-4-(4-pyridyl)thiazole is used (yield; 61%).

IR$_{max}$ cm$^{-1}$ (KBr): 3421, 1774, 1701, 1604, 342, 1275

$^1$H-NMR δ (CDCl$_3$): 1.16 (3H, d, J=7.3 Hz), 1.34 (3H, d, J=6.3 Hz), 3.32 (1H, dd, J=3.0 Hz and 6.6 Hz), 3.65 (1H, m), 4.30 (2H, m), 5.31 (1H, d, J=13.9 Hz),5.55 (1H, d, J=13.9 Hz), 7.68 (2H, d, J=8.9Hz), 7.78 (3H,s), 8.25 (2H, d, J=8.9 Hz), 8.71 (2H, d, J=8.9 Hz)

b) (4R,5S,6S,8R)-p-Nitrobenzyl-3-(4-(4-pyridyl)thiazol-2-ylthio)-4-methyl6-(6(1-hydroxyethyl)-1-azabicyclo [3.2.0]hept-2-en-7-one-2-carboxylate (48.1 g, 89.4 mmol) and 2-iodoacetamide (82.6 g) are refluxed for 7 hours in a mixture of acetone (400 ml) and THF (800 ml). The reaction solution is cooled with ice and the precipitated crystals are collected by filtration, washed with acetone, and dried under reduced pressure to give (4R,5S,6S,8R)

-p-nitrobenzyl-3-(4(1-(1-(aminocarbonylmethyl)pyridinium-4-yl)thiazol-2-ylthio)-4-methyl-6-(1-hydroxyethyl)-1-azabicyclo[3.2.0]hept-2-en-7-one-2-carboxylate iodide (62.3 g, yield; 96%).

IR$_{max}$ cm$^{-1}$ (KBr): 3424, 1786, 1693, 1639, 1519, 1347
$^1$H-NMR δ (DMSO d-6): 1.03 (3H, d, J=7.3 Hz), 1.10 (3H, d, J=6.3 Hz), 3.44 (1H, dd, J=3.3 Hz and 5.6 Hz), 3.64 (1H, m), 4.00 (1H, m), 4.37 (1 J=3.3 Hz and 10.6 Hz), 5.08 (1H, d, J=5.0 Hz, —OH), 5.38 (2H, s), 5.40 (1H, d, J=13.9 Hz), 5.52 (1H, d, J=13.9 Hz), 7.74 (2H, d, J=8.6 Hz), 8.04 (1H, s) 8.25 (2H, d,J=8.64 (2H, d, J=7.0 Hz), 8.98 (2H, d, J=7.0 Hz), 9.14 (1H, s) c)

In the same deprotection procedure as in Example 1, (4R,5S,6S,8R)-3(4-(1-(aminocarbonylmethyl)pyridinium-4-yl)thiazol-2-ylthio)-4-methyl-6-(1-hydroxyethyl)-1-azabicyclo[3.2.0]hept-2-en-7-one-2-carboxylate is obtained as yellow amorphous from (4R,5S,6S,8R)-p-nitrobenzyl-3-(4-(1-(aminocarbonylmethyl)pyridinium-4-yl)thio-4-methyl-6-(1-hydroxyethyl)-1-azabicyclo[3.2.0]hept-2-en-7-one-2-carboxylate iodide.

UV$_{max}$ nm (H$_2$O): 310, 282 (sh)
IR$_{max}$ cm$^{-1}$ (KBr): 3424, 1762, 1602, 1388
$^1$H-NMR δ (D$_2$O): 1.07 (3H, d, J=7.3 Hz), 1.26 (3H, d, J=6.6 Hz), 3.59 (2H, m), 4.27 (2H, m), 5.51 (2H, s), 8.38 (2H, d, J=7.3 Hz), 8.60 (1H, s), 8.77 (2H, d, J=7.3 Hz)

EXAMPLE 13

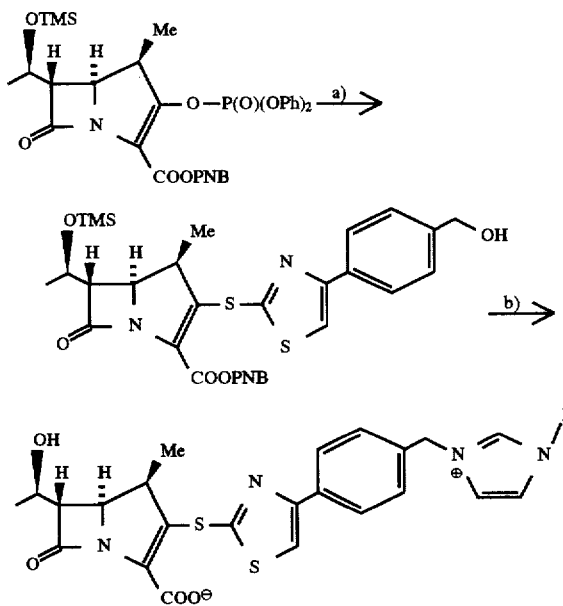

a) (4R,5S,6S,8R)-p-Nitrobenzyl-3-(4-(4-hydroxymethylphenyl)thiazol-2-ylthio)-4-methyl-6-(trimethylsilyloxy)ethyl)-1-azabicyclo[3.2.0]hept-2-en-7-one-2-carboxylate is obtained as pale yellow oil in the same manner as in Example 10 except that 2-mercapto-4-(4-hydroxymethylphenyl)thiazole is used (yield; 46%).
IR$_{max}$ cm$^{-1}$ (KBr): 3400, 1770, 1591, 1520, 1346
$^1$H-NMR δ (CDCl$_3$): 0.11 (9H, s), 1.13 (3H, d, J=7.3 Hz), 1.27 (3H, d, J=6.3 Hz), 3.26 (1H, dd, J=3.0 Hz and 5.6 Hz), 3.60 (1H, m), 4.25 (2H, m), 4.74 (2H, b.r.s), 5.31 (1H, d, J=13.9 Hz), 5.50 (1H, d, J=13.9 Hz), 7.44 (2H, d, J=8.3 Hz), 7.56 (1H, s), 7.68 (2H, d, J=8.6 Hz), 7.89 (2H, d, J=8.3 Hz), 8.22 (2H, d, J=8.6 Hz)

b) To a solution of (4R,5S,6S,8R)-p-nitrobenzyl-3-(4-(4-hydroxymethylphenyl)thiazol-2-ylthio)-4-methyl-6-(1-(trimethylsilyoxy)ethyl)-1-azabicyclo[3.2.0]hept-2-en-7-one-2-carboxylate (286 mg, 0.46 mmol) and 1-methylimidazole (75 mg, 0.91 mmol) in dichloromethane (3.0 ml) is added dropwise anhydrous trifluoromethanesulfonic acid (154 mg, 0.54 mmol) under ice-cooling. cooling. The mixture is stirred at the same temperature for three hours, and the reaction solution is diluted with dichloromethane, washed with water, dried over magnesium sulfate, and evaporated to remove the solvent. The residue is subjected to deprotection procedure as in Example 1 to give (4R,5S,6S,8R)-3-(4-(4-(4-methylimidazolium-1-yl)methylphenyl)thiazol-2-ylthio)-4-methyl-6-(1-hydroxyethyl)-1-azabicyclo[3.2.0]hept-2-en-7-one-2-carboxylate as white amorphous.

UV$_{max}$ nm (H$_2$O): 315 (sh), 266
IR$_{max}$ cm$^{-1}$ (KBr): 3423, 1751, 1653,1614, 1394
$^1$H-NMR δ (D$_2$O): 0.90 (3H, d, J=7.3 Hz), 1.17 (3H, d, J=6.3 Hz), 3.09 (1H, m), 3.30 (1H, dd, J=2.6 Hz and 5.6 Hz), 3.89 (3H, s), 4.07 (1H, dd, J=2.6 Hz and 9.6 Hz), 4.15 (1H, m), 5.51 (2H, s), 7.43 (2H, d, J=8.3 Hz), 7.45 (1H, br.s), 7.52 (1H, br.s), 7.73 (2H, d, J=8.3 Hz), 7.75 (1H, s), 8.86 (1H, br.s)

The compounds of Examples 14–52 are obtained in the same procedures or a combination thereof as used in Examples 1 to 13.

EXAMPLE 14

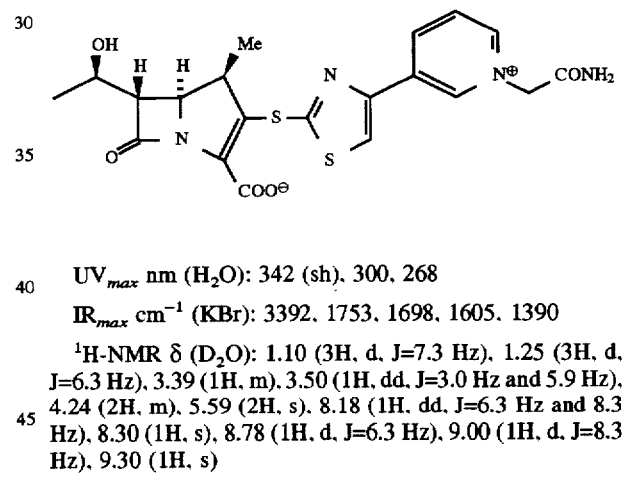

UV$_{max}$ nm (H$_2$O): 342 (sh), 300, 268

IR$_{max}$ cm$^{-1}$ (KBr): 3392, 1753, 1698, 1605, 1390

$^1$H-NMR δ (D$_2$O): 1.10 (3H, d, J=7.3 Hz), 1.25 (3H, d, J=6.3 Hz), 3.39 (1H, m), 3.50 (1H, dd, J=3.0 Hz and 5.9 Hz), 4.24 (2H, m), 5.59 (2H, s), 8.18 (1H, dd, J=6.3 Hz and 8.3 Hz), 8.30 (1H, s), 8.78 (1H, d, J=6.3 Hz), 9.00 (1H, d, J=8.3 Hz), 9.30 (1H, s)

EXAMPLE 15

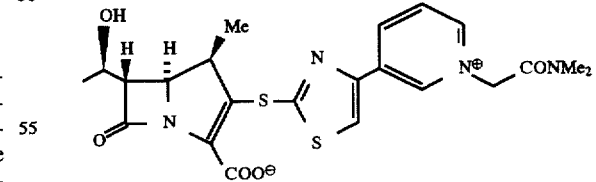

UV$_{max}$ nm (H$_2$O): 292, 240 (sh)

IR$_{max}$ cm$^{-1}$ (KBr): 3421, 1758, 1662, 1601, 1386

$^1$H-NMR δ (D$_2$O):1.11 (3H, d, J=7.3 Hz), 1.26 (3H, d, J=6.3 Hz), 3.02 (3H, s), 3.18 (3H, s), 3.40 (1H, m), 3.50 (1H, dd, J=3.0 Hz and 5.9 Hz), 4.24 (2H, m), 5.82 (2H, s), 8.19 (1H, dd, J=5.9 Hz and 7.9 Hz), 8.32 (1H, s), 8.72 (1H, d, J=5.9 Hz), 9.01 (1H, d, J=7.9 Hz), 9.25 (1H, s)

EXAMPLE 16

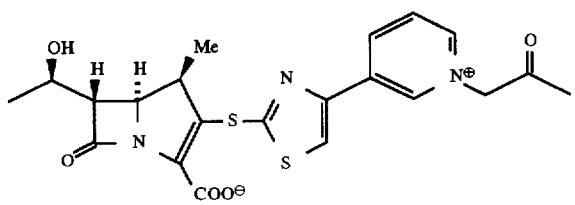

UV$_{max}$ nm (H$_2$O): 301, 271 (sh), 233 (sh)

IR$_{max}$ cm$^{-1}$ (KBr): 3410, 1759, 1600, 1384

$^1$H-NMR δ (D$_2$O): 1.06 (3H, d, =7.3 Hz), 1.24 (3H, d, J=6.3 Hz), 2.46 (3H, s), 3.39 (1H, m), 3.48 (1H, dd, J=3.0 Hz and 5.9 Hz), 4.23 (2H, m), 4.81 (2H, s), 8.16 (1H, dd, J=6.3 Hz and 8.3 Hz), 8.25 (1H, s), 8.63 (1H, d, J=6.3 Hz), 8.95 (1H, d, J=8.3 Hz), 9.13 (1H, s)

EXAMPLE 17

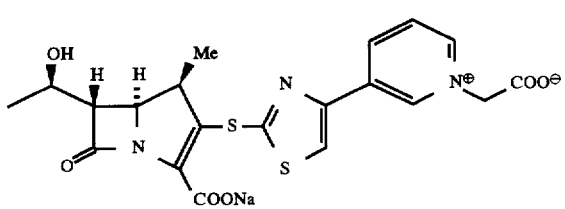

UV$_{max}$ nm (H$_2$O): 301, 271 (sh)

IR$_{max}$ cm$^{-1}$ (KBr): 3418, 1752, 1636, 1374

$^1$H-NMR δ (D$_2$O): 1.13 (3H, d, J=7.3 Hz), 1.28 (3H, d, J=6.3 Hz), 3.42 (1H, m), 3.52 (1H, dd, J=3.0 Hz and 5.9 Hz), 4.28 (2H, m), 5.32 (2H, s), 8.17 (1H, d, J=5.3 Hz and 7.9 hz), 8.31 (1H, d, J=1.0 Hz), 8.76 (1H, dd, J=1.0 Hz and 5.3 Hz), 8.96 (1H, d, J=7.9 Hz), 9.28 (1H, s)

EXAMPLE 18

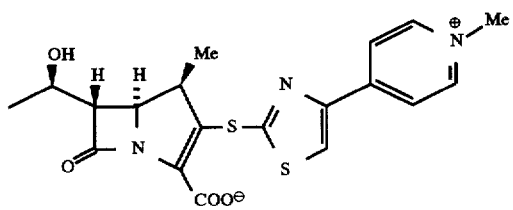

UV$_{max}$ nm (H$_2$O): 312, 285 (sh)

IR$_{max}$ cm$^{-1}$ (KBr): 3380, 1762, 1636, 1605, 1388

$^1$H-NMR δ (D$_2$O): 1.12 (3H, d, J=7.3 Hz), 1.27 (3H, d, J=6.3 Hz), 3.44 (1H, m), 3.53 (1H, dd, J=3.0 Hz and 5.3 Hz), 4.27 (2H, m), 4.38 (3H, s), 8.40 (2H, d, J=6.9 Hz), 8.61 (1H, s), 8.78 (2H, d, J=6.9 Hz)

EXAMPLE 19

19-a)

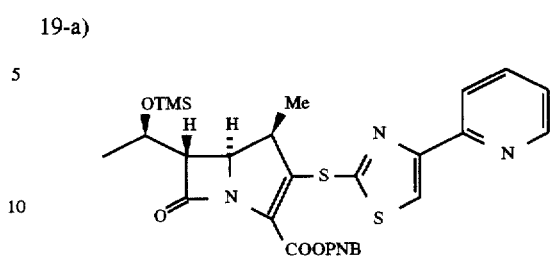

IR$_{max}$ cm$^{-1}$ (neat): 1780, 1521, 1346

$^1$H-NMR δ (CDCl$_3$): 0.11 (9H, s), 1.13 (3H, d, J=7.3 Hz), 1.22 (3H, d, J=6.3 Hz), 3.27 (1H, dd, J=3.0 Hz and 5.6 Hz), 3.53 (1H, m), 4.26 (2H, m), 5.32 (1H, d, J=14.0 Hz), 5.53 (1H, d, J=14.0 Hz), 7.20 (1H, m), 7.68 (2H, d, J=8.6 Hz), 7.80 (1H, m), 8.12 (1H, d, J=7.9 Hz), 8.20 (1H, d), 8.23 (2H, d, J=8.6 Hz), 8.63 (1H, d, J=5.0 Hz)

19-b)

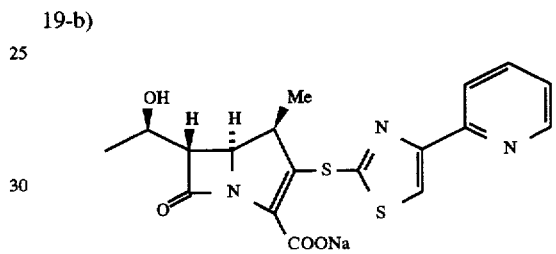

UV$_{max}$ nm (H$_2$O): 321 (sh), 291

IR$_{max}$ cm$^{-1}$ (KBr): 3402, 1758, 1603, 1394

$^1$H-NMR δ (D$_2$O): 1.12 (3H, d, J=7.6 Hz), 1.26 (3H, d, J=6.3 Hz), 3.37 (1H, m), 3.49 (1H, dd, J=2.6 Hz and 5.9 Hz), 4.26 (2H, m), 7.47 (1H, m), 7.99 (2H, m), 8.17 (1H, s), 8.58 (1H, d, J=5.0 Hz)

EXAMPLE 20

20-a)

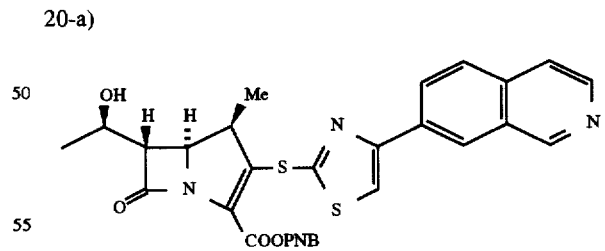

IR$_{max}$ cm$^{-1}$ (neat): 3388, 1734, 1608, 1522, 1346

$^1$H-NMR δ (CDCl$_3$): 1.16 (3H, d, J=7.3 Hz), 1.31 (3H, d, J=6.3 Hz), 3.31 (1H, dd, J=2.6 Hz and 6.6 Hz), 3.68 (1H, m), 4.25 (1H, m), 4.34 (1H, dd, J=2.6 Hz and 9.9Hz), 5.30 (1H, d, J=13.5 Hz), 5.53 (1H, d, J=13.5 Hz), 7.65 (1H, d, J=5.6 Hz), 7.65 (2H, d, J=8.6 Hz), 7.74 (1H, s), 7.88 (1H, d, J=8.6 Hz), 8.16 (1H, dd, J=2.0 Hz and 8.6 Hz), 8.20 (2H, d, J=8.6 Hz), 8.53 (1H, d, J=5.6 Hz), 8.53 (1H, br.s), 9.31 (1H, s)

20-b)

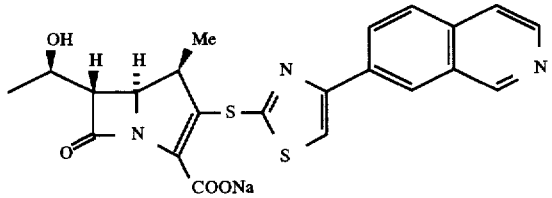

UV$_{max}$ nm (H$_2$O): 300, 291 (sh), 248 (sh), 223
IR$_{max}$ cm$^{-1}$ (KBr): 3448, 1751, 1603, 1496, 1394
$^1$H-NMR δ (D$_2$O): 1.11 (3H, d, J=6.9 Hz), 1.27 (3H, d, J=6.3 Hz), 3.31 (1H, m), 3.49 (1H, dd, J=2.6 Hz and 5.9 Hz), 4.26 (2H, m), 7.65 (1H, d, J=5.3 Hz), 7.78 (1H, d, J=9.9 Hz), 7.80 (1H, s), 7.89 (1H, d, J=9.9 Hz), 8.02 (1H, br.s), 8.25 (1H, d, J=5.3 Hz), 8.95 (1H, s)

EXAMPLE 21

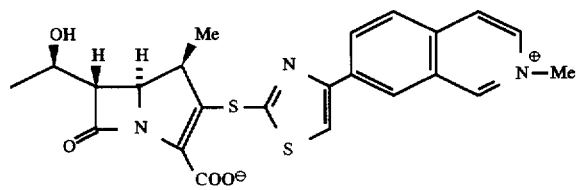

UV$_{max}$ nm (H$_2$O): 305, 265 (sh), 253 (sh), 240
IR$_{max}$ cm$^{-1}$ (KBr): 3421, 1757, 1602, 1388
$^1$H-NMR δ (D$_2$O): 1.06 (3H, d, J=7.3 Hz), 1.23 (3H, d, J=6.6 Hz), 3.34 (1H, m), 3.47 (1H, dd, J=2.0 Hz and 5.6 Hz), 4.22 (2H, m), 4.54 (3H, s), 8.15 (1H, s), 8.24 (1H, d, J=8.3 Hz), 8.37 (1H, d, J=6.6 Hz), 8.46 (2H, m), 8.65 (1H, s), 9.67 (1H, s)

EXAMPLE 22

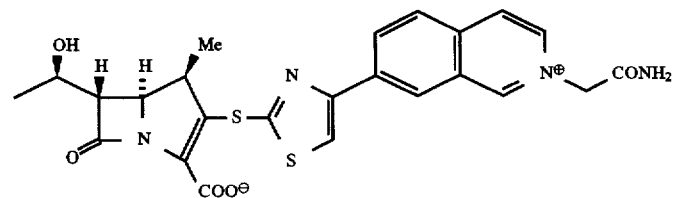

UV$_{max}$ nm (H$_2$O): 300, 271, 242

IR$_{max}$ cm$^{-1}$ (KBr): 3392, 1758, 1697, 1600, 1388

$^1$H-NMR δ (D$_2$O): 1.02 (3H, d, J=7.3 Hz), 1.22 (3H, d, J=6.3 Hz), 3.33 (1H, m), 3.46 (1H, dd, J=2.6 Hz and 5.9 Hz), 4.21 (2H, m), 5.64 (2H, s), 7.97 (1H, s), 8.11 (1H, d, J=8.9 Hz), 8.30 (2H, m), 8.43 (2H, m), 9.62 (1H, s)

EXAMPLE 23

23-a)

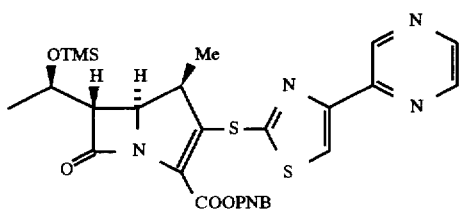

IR$_{max}$ cm$^{-1}$ (neat): 1772, 1521, 1345

$^1$H-NMR δ (CDCl$_3$): 0.12 (9H, s), 1.15 (3H, d, J=7.3 Hz), 1.22 (3H, d, J=5.9 Hz), 3.29 (1H, dd, J=3.0 Hz and 5.3 Hz), 3.60 (1H, m), 4.27 (2H, m), 5.32 (1H, d, J=13.9 Hz), 5.53 (1H, d, J=13.9 Hz), 7.69 (2H, d, J=8.9 Hz), 8.23 (3H, m), 8.58 (2H, m), 9.36 (1H, d, J=1.3 Hz)

23-b)

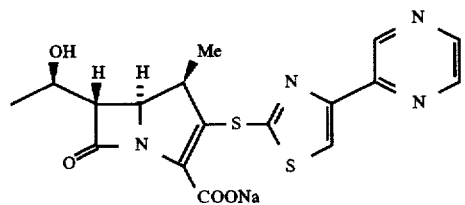

UV$_{max}$ nm (H$_2$O): 311, 248 (sh)

IR$_{max}$ cm$^{-1}$ (KBr): 3416, 1760, 1600, 1393

$^1$H-NMR δ (D$_2$O): 1.12 (3H, d, J=7.3 Hz), 1.26 (3H, d, J=6.3 Hz), 3.40 (1H, m), 3.51 (1H, dd, J=2.6 Hz and 5.9 Hz), 4.29 (2H, m), 8.34 (1H, s), (1H, d, J=2.6 Hz), 8.68 (1H, dd, J=1.7 Hz and 2.6 Hz), 9.15 (1H, d, J=1.7 Hz)

EXAMPLE 24

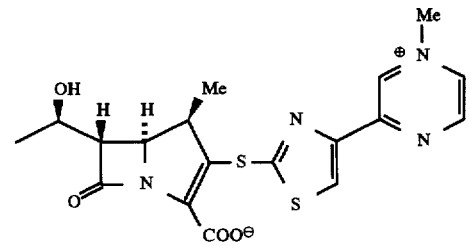

UV$_{max}$ nm (H$_2$O): 306
IR$_{max}$ cm$^{-1}$ (KBr): 3406, 1756, 1600, 1391
$^1$H-NMR δ (D$_2$O): 1.15 (3H, d, J=7.3 Hz), 1.27 (3H, d, J=6.3 Hz), 3.60 (2H, m), 4.29 (2H, m), 4.58 (3H, s), 8.69 (1H, s), 8.80 (1H, d, J=3.60 (1H, m), 9.45 (1H, br.s)

EXAMPLE 25
25-a)
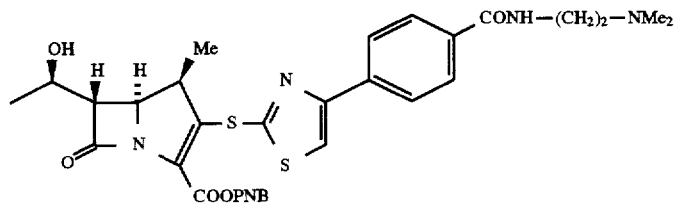
IR$_{max}$ cm$^{-1}$ (neat): 3375, 1772, 1734, 1652, 1521, 1347
$^1$H-NMR δ (CDCl$_3$): 1.13 (3H, d, J=7.3 Hz), 1.37 (3H, d, J=6.3 Hz), 2.35 (6H, s), 2.65 (2H, m), 3.30 (1H, dd, J=3.0 Hz and 6.9 Hz), 3.59 (3H, m), 4.28 (2H, m), 5.30 (1H, d, J=13.5 Hz), 5.54 (1H, d, J=13.5 Hz), 7.54 (2H, d, J=8.9 Hz), 7.68 (2H, d, J=8.9 Hz), 7.90 (3H, m), 8.24 (2H, d, J=8.9 Hz)
25-b)
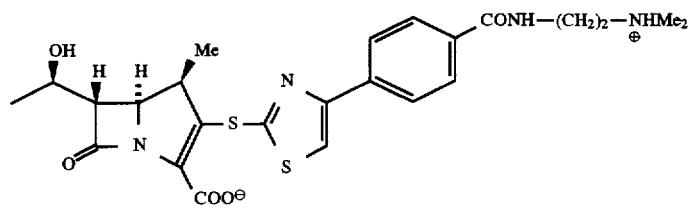
UV$_{max}$ nm (H$_2$O): 288
IR$_{max}$ cm$^{-1}$ (KBr): 3421, 1762, 1609, 1560, 1388
$^1$H-NMR δ (D$_2$O): 0.88 (3H, d, J=7.3 Hz), 1.14 (3H, d, J=6.3 Hz), 3.00 (6H, s), 3.13 (1H, m), 3.29 (1H, dd, J=3.0 Hz and 5.9 Hz), 3.46 (2H, m), 3.83 (2H, m), 3.95 (1H, dd, J=3.0 Hz and 9.2 Hz), 4.10 (1H, m), 7.80 (5H, s)
$^1$H-NMR δ (D$_2$O): 0.84 (3H, d, J=7.3 Hz), 1.16 (3H, d, J=6.3 Hz), 3.12 (1H, m), 3.26 (9H, s), 3.27 (1H, m), 3.62 (2H, m), 3.89 (2H, m), 4.07 (1H, d, J=2.3 Hz and 10.2 Hz), 4.13 (1H, m), 7.65 (5H, m)
EXAMPLE 26
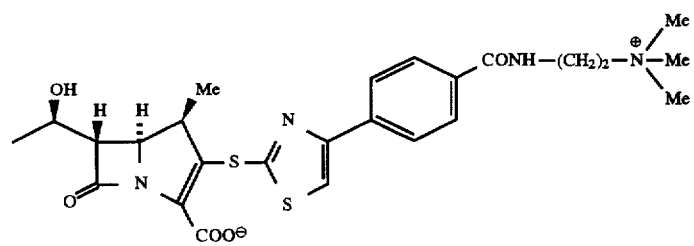
UV$_{max}$ nm (H$_2$O): 285
IR$_{max}$ cm$^{-1}$ (KBr): 3419, 1762, 1654, 1608, 1560, 1388
EXAMPLE 27
27-a)
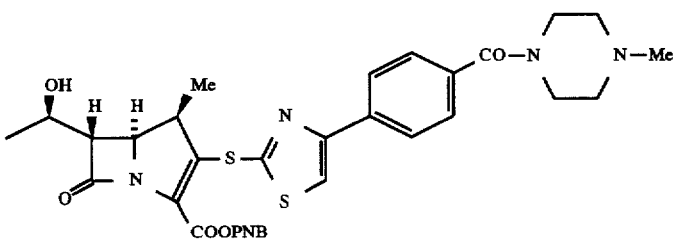
IR$_{max}$ cm$^{-1}$ (neat): 3375, 1772, 1616, 1522, 1457, 1346

¹H-NMR δ (CDCl₃): 1.14 (3H, d, J=7.3 Hz), 1.32 (3H, d, J=6.3 Hz), 2.33 (3H, s), 2.43 (4H, m), 3.30 (1H, dd, J=3.0 Hz and 6.6 Hz), 3.48 (2H, m), 3.64 (1H, m), 3.79 (2H, m), 4.27 (2H, m), 5.30 (1H, d, J=13.7 Hz), 5.54 (1H, d, J=13.7 Hz), 7.49 (2H, m), 7.64 (1H, s), 7.68 (2H, d, J=8.9 Hz), 7.93 (2H, d, 8.6 Hz), 8.24 (2H, d, J=8.9 Hz)

IR$_{max}$ cm⁻¹ (KBr): 3420, 1758, 1696, 1609, 1448, 1387
¹H-NMR δ (D₂O): 1.10 (3H, d, J=7.3 Hz), 1.22 (3H, d, J=6.3 Hz), 3.25 (1H, m), 3.42 (1H, dd, J=2.6 Hz and 5.6Hz), 3.45 (3H, s), 3.60–4.15 (8H, m), 4.23 (2H, m), 4.34 (2H, s), 7.54 (2H, d, J=8.6 Hz), 7.84 (2H, d, J=8.6 Hz), 7.88 (1H,s)

EXAMPLE 30

30-a)

27-b)

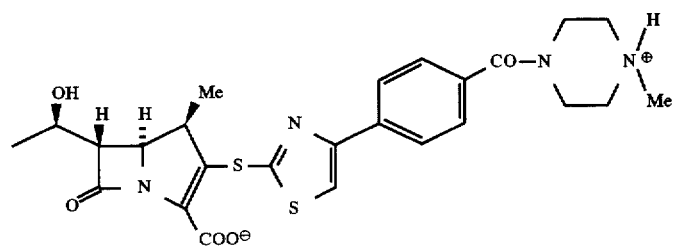

UV$_{max}$ nm (H₂O): 332 (sh), 287
IR$_{max}$ cm⁻¹ (KBr): 3424, 1758, 1654, 1457, 1387
¹H-NMR δ (D₂O): 1.06 (3H, d, J=6.6 Hz), 1.24 (3H, d, J=6.3 Hz), 2.78 (3H, s), 3.00–3.40 (5H, m), 3.45 (1H, m), 3.65–4.10 (4H, m), 4.26 (2H, m), 7.53 (2H, d, J=8.3 Hz), 7.88 (2H, d, J=8.3 Hz), 7.93 (1H, s)

EXAMPLE 28

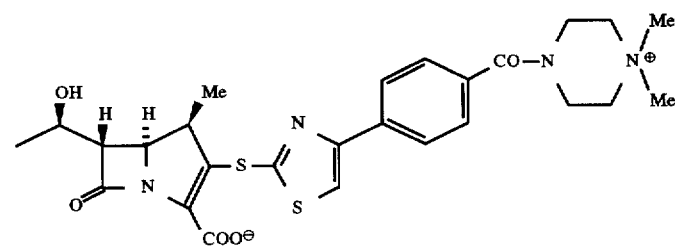

UV$_{max}$ nm (H₂O): 318 (sh), 278
IR$_{max}$ cm⁻¹ (KBr): 3422, 1752, 1620, 1560, 1457
¹H-NMR δ (D₂O): 0.92 (3H, d, J=7.3 Hz), 1.19 (3H, d, J=6.3 Hz), 3.19 (1H, m), 3.30 (6H, s), 3.36 (1H, dd, J=2.6 Hz and 5.6 Hz), 3.57 (4H, m), 3.19 (2H, m), 4.15 (4H, m), 7.50 (2H, d, J=8.3 Hz), 7.79 (2H, d, J=8.3 Hz), 7.81 (1H, s)

EXAMPLE 29

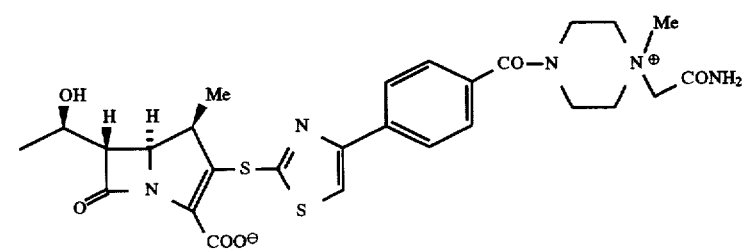

UV$_{max}$ nm (H₂O): 319 (sh), 274

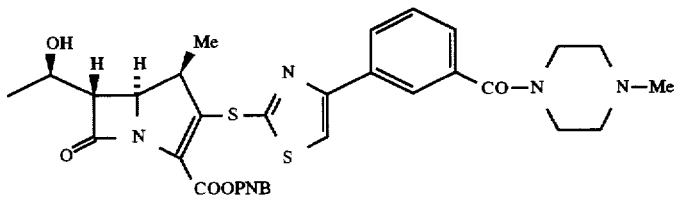

IR$_{max}$ cm$^{-1}$ (neat): 3430, 1777, 1620, 1524, 1443, 1346
$^1$H-NMR δ (CDCl$_3$):1.14 (3H, d, J=7.3 Hz), 1.34 (3H, d, J=6.3 Hz), 2.33 (3H, s), 2.37 (2H, m), 2.51 (2H, m), 3.30 (1H, dd, J=3.0 Hz and 6.9 Hz), 3.49 (2H, m), 3.69 (1H, m), 3.80 (2H, m), 4.27 (2H, m), 5.30 (1H, d, J=13.5 Hz), 5.54 (1H, d, J=13.5 Hz), 7.45 (2H, m), 7.62 (1H, s), 7.68 (2H, d, J=8.9 Hz), 7.94 (2H, m), 8.24 (2H, d, J=8.9 Hz)

30-b)

$^1$H-NMR δ (D$_2$O): 1.04 (3H, d, J=7.3 Hz), 1.24 (3H, d, J=6.6 Hz), 3.28 (1H, m), 3.30 (6H, s), 3.44 (1H, dd, J=3.0 Hz and 5.9 Hz), 3.53 (2H, m), 3.65 (2H, m), 3.93 (2H, m), 4.20 (4H, m), 7.48 (1H, d, J=7.6 Hz), 7.60 (1H, t, J=7.6 Hz), 7.85 (1H, s), 7.90 (1H, s), 7.91 (1H, d, J=7.6 Hz)

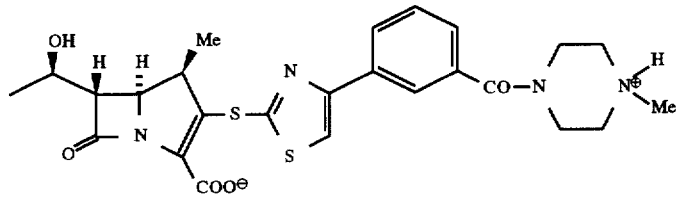

UV$_{max}$ nm (H$_2$O): 312 (sh), 262
IR$_{max}$ cm$^{-1}$ (KBr): 3427, 1762, 1603, 1457, 1388
$^1$H-NMR δ (D$_2$O):1.08 (3H, d, J=7.3 Hz), 1.25 (3H, d, J=6.6 Hz), 2.36 (3H, s), 2.53 (2H, m), 2.69 (2H, m), 3.32 (1H, m), 3.51 (3H, m), 3.81 (2H, m), 4.24 (2H, m), 7.45 (1H, dd, J=1.3 Hz and 7.9 Hz), 7.59 (1H, t, J=7.9 Hz), 7.82 (1H, d, J=1.3 Hz), 7.93 (2H, m)

EXAMPLE 31

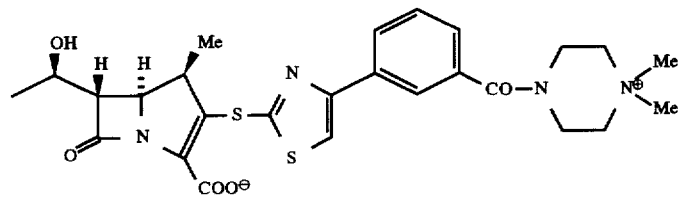

UV$_{max}$ nm (H$_2$O): 315 (sh), 265 (sh)
IR$_{max}$ cm$^{-1}$ (KBr): 3424, 1752, 1602, 1457, 1382

EXAMPLE 32

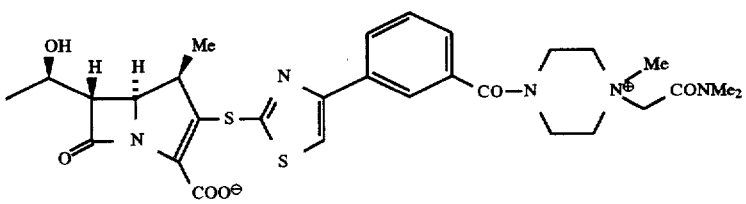

UV$_{max}$ nm (H$_2$O): 314 (sh), 266 (sh)

IR$_{max}$ cm$^{-1}$ (KBr): 3419, 1758, 1654, 1604, 1452, 1386

$^1$H-NMR δ (D$_2$O): 1.07 (3H, d, J=7.3 Hz), 1.25 (3H, d, J=6.3 Hz), 2.98 (3H, s), 3.06 (3H, s), 3.29 (1H, m), 3.50 (4H, m), 3.70–4.15 (8H, m), 4.23 (2H, m), 4.56 (2H, s), 7.50 (1H, d, J=7.9 Hz), 7.62 (1H, t, J=7.9 Hz), 7.89 (1H, s), 7.95 (1H, s), 7.96 (1H, d, J=7.9 Hz)

EXAMPLE 33

33-a)

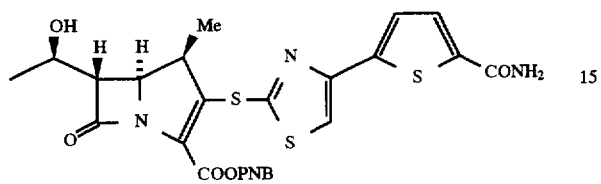

IR$_{max}$ cm$^{-1}$ (KBr): 3386, 1751, 1709, 1661, 1604, 1522, 1452, 1383

$^1$H-NMR δ (DMSO d-6): 1.05 (3H, d, J=7.3 Hz), 1.11 (3H, d, J=6.3 Hz), 3.39 (1H, dd, J=3.0 Hz and 5.9 Hz), 3.53 (1H, m), 4.00 (1H, m), 4.31 (1H, dd, J=3.0 Hz and 10.3 Hz), 5.07 (1H, d, J=5.0 Hz, —OH), 5.40 (1H, d, J=13.9 Hz), 5.51 (1H, d, J=13.9 Hz), 7.46 (1H, br., —NH), 7.61 (1H, d, J=4.0 Hz), 7.73 (1H, d, J=4.0 Hz), 7.75 (2H, d, J=8.9 Hz), 8.02 (1H, br., —NH), 8.25 (2H, d, J=8.9 Hz), 8.29 (1H, s)

33-b)

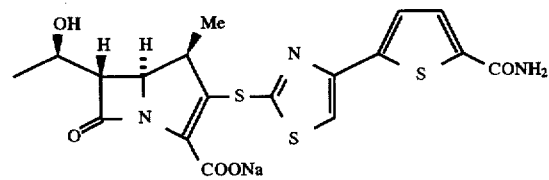

UV$_{max}$ nm (H$_2$O): 316

IR$_{max}$ cm$^{-1}$ (KBr): 3415, 1752, 1654, 1598, 1451, 1394

$^1$H-NMR δ (D$_2$O): 1.08 (3H, d, J=7.3 Hz), 1.27 (3H, d, J=6.3 Hz), 3.31 (1H, m), 3.49 (1H, dd, J=3.0 Hz and 5.9 Hz), 4.27 (2H, m), 7.36 (1H, d, J=4.0 Hz), 7.59 (1H, d, J=4.0 Hz), 7.80 (1H, s)

EXAMPLE 34

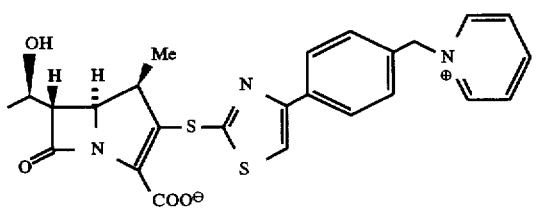

UV$_{max}$ nm (H$_2$O): 318 (sh), 279 (sh), 268 (sh), 261

IR$_{max}$ cm$^{-1}$ (KBr): 3406, 1758, 1599, 1387

$^1$H-NMR δ (D$_2$O): 0.94 (3H, d, J=7.3 Hz), 1.19 (3H, d, J=6.3 Hz), 3.14 (1H, m), 3.38 (1H, dd, J=2.6 Hz and 5.6 Hz), 4.11(1H, dd, J=2.6 Hz and 9.6 Hz), 4.18 (1H, m), 5.86 (2H, s), 7.53 (2H, d, J=8.3 Hz), 7.79 (2H, d, J=8.3 Hz), 7.82 (1H, s), 8.09 (2H, t, J=6.9 Hz), 8.56 (1H, t, J=7.9 Hz), 8.98 (2H, d, J=6.6 Hz)

EXAMPLE 35

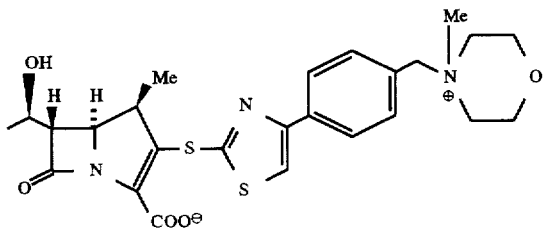

UV$_{max}$ nm (H$_2$O): 320 (sh), 272

IR$_{max}$ cm$^{-1}$ (KBr): 3396, 1756, 1601, 1384

$^1$H-NMR δ (D$_2$O): 0.95 (3H, d, J=7.3 Hz), 1.19 (3H, d, J=6.3 Hz), 3.17 (3H, s), 3.20 (1H, m), 3.37 (1H, dd, J=2.0 Hz and 5.9 Hz), 3.46 (2H, m), 3.67 (2H, m), 4.14 (6H, m), 4.68 (2H, s), 7.61 (2H, d, J=8.3 Hz), 7.86 (2H, d, J=8.3 Hz), 7.91 (1H, s)

EXAMPLE 36

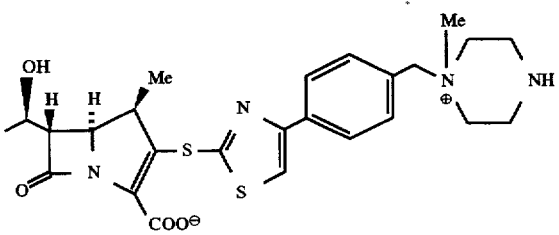

UV$_{max}$ nm (H$_2$O): 316 (sh), 269

IR$_{max}$ cm$^{-1}$ (KBr): 3396, 1756, 1601, 1382

$^1$H-NMR δ (D$_2$O): 1.00 (3H, d, J=7.3 Hz), 1.21 (3H, d, J=6.6 Hz), 3.10 (3H, s), 3.24 (5H, m), 3.40 (3H, m), 3.52 (2H, m), 4.19 (2H, m), 4.64 (2H, s,) 7.61 (2H, d, J=8.3 Hz), 7.88 (2H, d, J=8.3 Hz), 7.94 (1H, s)

EXAMPLE 37

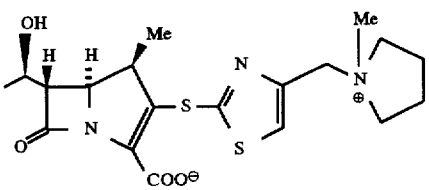

UV$_{max}$ nm (H$_2$O): 319 (sh), 268

IR max cm$^{-1}$ (KBr): 3422, 1752, 1607, 1376

$^1$H-NMR δ (D$_2$O): 0.99 (3H, d, J=7.3 Hz), 1.21 (3H, d, J=6.6 Hz), 2.28 (4H, m), 2.99 (3H, s), 3.24 (1H, m), 3.46 (3H, m), 3.64 (2H, m), 4.25 (2H, m), 4.55 (2H, s), 7.61 (2H, d, J=7.9 Hz), 7.86 (2H, d, J=7.9 Hz), 7.91 (1H, s)

EXAMPLE 38

38-a)

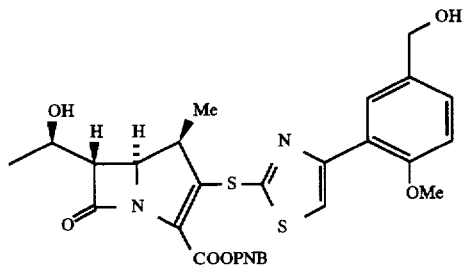

$^1$H-NMR δ (CDCl$_3$): 0.11 (9H, s), 1.12 (3H, d, J=7.3 Hz), 1.22 (3H, d, J=5.9 Hz), 1.81 (1H, t, J=5.9 Hz, —OH), 3.26 (1H, dd, J=3.0 Hz and 5.9 Hz), 3.53 (1H, m), 3.97 (3H, s), 4.27 (2H, m), 4.70 (2H, d, J=5.9 Hz), 5.31 (1H, d, J=13.5 Hz), 5.50 (1H, d, J=13.5 Hz), 7.01 (1H, d, J=8.6 Hz), 7.37 (1H, dd, J=2.3 Hz and 8.6 Hz), 7.68 (2H, d, J=8.9 Hz), 8.05 (1H, s), 8.20 (3H, m)

38-b)

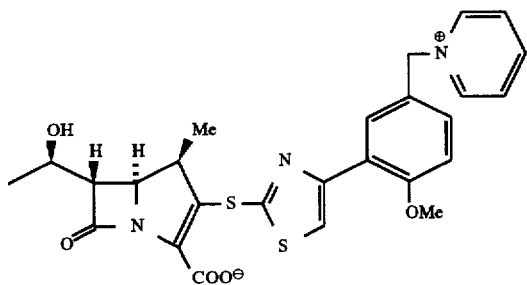

UV$_{max}$ nm (H$_2$O): 305, 259

IR$_{max}$ cm$^{-1}$ (KBr): 3416, 1761, 1605, 1498, 1383

$^1$H-NMR δ (D$_2$O): 0.86 (3H, d, J=6.9 Hz), 1.12 (3H, d, J=6.3 Hz), 3.06 (1H, m), 3.30 (1H, m), 3.83 (3H, s), 4.08 (2H, m), 5.72 (2H, s), 7.11 (1H, d, J=8.3 Hz), 7.46 (1H, d, J=8.3 Hz), 7.78 (2H, s), 7.97 (2H, t, J=6.6 Hz), 8.45 (1H, t, J=7.9 Hz), 8.87 (2H, d, J=6.6 Hz)

EXAMPLE 39

39-a)

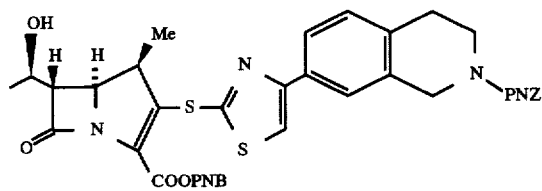

IR$_{max}$ cm$^{-1}$ (KBr): 3449, 1774, 1704, 1521, 1344

$^1$H-NMR δ (CDCl$_3$): 1.13 (3H, d, J=7.3 Hz), 1.32 (3H, d, J=6.3 Hz), 2.92 (2H, m), 3.30 (1H, dd, J=2.6 Hz and 6.6 Hz), 3.58 (1H, m), 3.78 (2H, m), 4.28 (2H, m), 4.75 (2H, m), 5.33 (1H, d, J=13.9 Hz), 5.53 (1H, d, J=13.9 Hz), 7.18 (1H, d, J=7.9 Hz), 7.54 (1H, d, J=7.9 Hz), 7.56 (1H, s), 7.68 (4H, d, J=8.3 Hz), 8.23 (4H, d, J=8.3 Hz)

39-b)

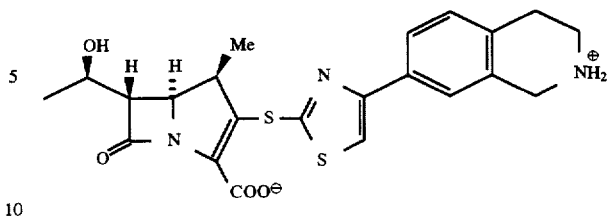

UV$_{max}$ nm (H$_2$O): 316 (sh), 263

IR max cm$^{-1}$ (KBr): 3396, 1762, 1598, 1383

$^1$H-NMR δ (D$_2$O): 0.93 (3H, d, J=6.6 Hz), 1.13 (3H, d, J=6.6 Hz), 3.10 (3H, m), 3.36 (1H, m), 3.48 (2H, m), 4.12 (2H, m), 4.34 (2H, br.s), 7.25 (1H, d, J=8.3 Hz), 7.50 (1H, s), 7.59 (1H, d, J=8.3 Hz), 7.73 (1H, s)

EXAMPLE 40

40-a)

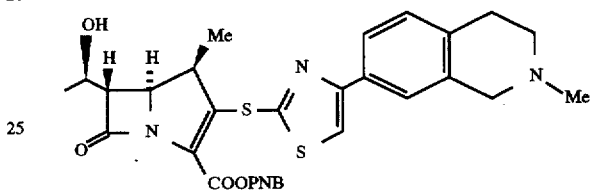

IR$_{max}$ cm$^{-1}$ (neat): 3381, 1772, 1700, 1522, 1346

$^1$H-NMR δ (CDCl$_3$): 1.12 (3H, d, J=7.3 Hz), 1.32 (3H, d, J=6.3 Hz), 2.49 (3H, s), 2.73 (2H, m), 2.95 (2H, m), 3.29 (1H, dd, J=2.6 Hz and 6.6 Hz), 3.58 (3H, m), 4.28 (2H, m), 5.30 (1H, d, J=13.9 Hz), 5.54 (1H, d, J=13.9 Hz), 7.10–7.65 (4H, m), 7.68 (2H, d, J=8.9 Hz), 8.24 (2H, d, J=8.9 Hz)

40-b)

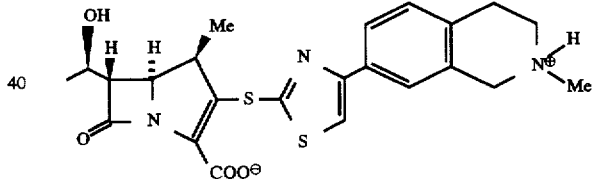

UV$_{max}$ nm (H$_2$O): 320 (sh), 265

IR$_{max}$ cm$^{-1}$ (KBr): 3422, 1759, 1600, 1472, 1387

$^1$H-NMR δ (D$_2$O): 1.01 (3H, d, J=7.6 Hz), 1.20 (3H, d, J=6.3 Hz), 2.99 (3H, s), 3.31 (3H, m), 3.41 (1H, dd, J=3.0 Hz and 5.9 Hz), 3.51 (2H, m), 4.18 (2H, m), 4.38 (2H, br.s), 7.35 (1H, d, J=7.9 Hz), 7.58 (1H, br.s), 7.70 (1H, d, J=7.9 Hz), 7.83 (1H, s)

EXAMPLE 41

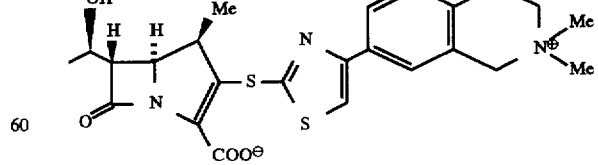

UV$_{max}$ nm (H$_2$O): 316 (sh), 265

IR$_{max}$ cm$^{-1}$ (KBr): 3428, 1758, 1600, 1387

$^1$H-NMR δ (D$_2$O): 1.04 (3H, d, J=7.3 Hz), 1.22 (3H, d, J=6.3 Hz), 3.25 (6H, s), 3.31 (3H, m), 3.43 (1H, dd, J=3.0

Hz and 5.6 Hz), 3.76 (2H, m), 4.20 (2H, m), 4.65 (2H, br.s),
7.42 (1H, d, J=7.9 Hz), 7.61 (1H, s), 7.77 (1H, d, 7.9 Hz),
7.87 (1H, s)

EXAMPLE 42

42-a)

¹H-NMR δ (CDCl₃): 1.12 (3H, d, J=7.3 Hz), 1.30 (3H, d, J=6.3 Hz), 3.30 (1H, dd, J=3.0 Hz and 6.6 Hz), 3.61 (1H, m), 4.22 (1H, m), 4.33 (1H, dd, J=3.9 Hz and 9.9 Hz), 5.29 (1H, d, J=13.9 Hz), 5.51 (1H, d, J=13.9 Hz), 7.21 (1H, d, J=15.8 Hz), 7.38 (4H, m), 7.66 (2H, d, J=8.9 Hz), 8.23 (2H, d, J=8.9 Hz), 8.59 (2H, m)

42-b)

UV$_{max}$ nm (H₂O): 322, 286 (sh)

IR$_{max}$ cm⁻¹ (KBr): 3393, 1764, 1621, 1389

¹H-NMR δ (D₂O): 1.11 (3H, d, J=7.3 Hz), 1.27 (3H, d, J=6.6 Hz), 3.35 (1H, m), 3.50 (1H, dd, J=3.0 Hz and 5.9 Hz), 4.25 (2H, m), 7.25 (1H, d, J=16.2 Hz), 7.41 (1H, d, J=16.2 Hz), 7.55 (2H, d, J=5.9 Hz), 7.72 (1H, s), 8.47 (2H, d, J=5.9 Hz)

EXAMPLE 43

UV$_{max}$ nm (H₂O): 312 (sh), 281, 256

IR$_{max}$ cm⁻¹ (KBr): 3319, 1766, 1606, 1392

¹H-NMR δ (D₂O): 0.97 (3H, d, J=7.3 Hz), 1.30 (3H, d, J=6.3 Hz), 2.95 (1H, m), 3.24 (4H, s), 3.45 (1H, dd, J=2.6 Hz and 5.9 Hz), 4.18 (1H, dd, J=2.6 Hz and 9.6 Hz), 4.26 (1H, m), 7.29 (1H, s), 7.53 (2H, d, J=6.3 Hz), 8.48 (2H, d, J=6.3 Hz)

EXAMPLE 44

UV$_{max}$ nm (H₂O): 330, 285 (sh)

IR max cm⁻¹ (KBr): 3374, 1759, 1621, 1384

¹H-NMR δ (D₂O): 1.08 (3H, d, J=7.3 Hz), 1.24 (3H, d, J=6.6 Hz), 3.37 (1H, m), 3.44 (1H, dd, J=3.0 Hz and 6.3 Hz), 4.24 (2H, m), 4.32 (3H, s), 7.40 (1H, d, J=16.2 Hz), 7.73 (1H, d, J=16.2 Hz), 7.92 (1H, s), 8.06 (2H, d, J=6.9 Hz), 8.61 (2H, d, J=5.9 Hz)

EXAMPLE 45

UV$_{max}$ nm (H₂O): 355, 321 (sh), 296 (sh), 286 (sh)

IR$_{max}$ cm⁻¹ (KBr): 3316, 1759, 1696, 1619, 1389

¹H-NMR δ (D₂O): 1.06 (3H, d, J=7.3 Hz), 1.24 (3H, d, J=6.3 Hz), 3.37 (1H, m), 3.49 (1H, dd, J=3.0 Hz and 5.9 Hz), 4.25 (2H, m), 5.43 (2H, s), 7.40 (1H, d, J=15.8 Hz), 7.75 (1H, d, J=15.8 Hz), 7.93 (1H, s), 8.09 (2H, d, J=6.9 Hz), 8.61 (2H, d, J=6.9 Hz)

EXAMPLE 46

46-a)

¹H-NMR δ (CDCl₃): 1.08 (3H, d, J=7.3 Hz), 1.32 (3H, d, J=6.3 Hz), 2.12 (3H, s), 3.29 (1H, dd, J=3.0 Hz and 6.9 Hz), 3.52 (1H, m), 4.30 (2H, m), 5.21 (2H, s), 5.27 (1H, d, J=13.9 Hz), 5.51 (1H, d, J=13.9 Hz), 7.39 (1H, s), 7.66 (2H, d, J=8.9 Hz), 8.22 (2H, d, J=8.9 Hz)

46-b)

UV$_{max}$ nm (H₂O): 308, 258 (sh)

IR$_{max}$ cm⁻¹ (KBr): 3412, 1745, 1605, 1393

¹H-NMR δ (D₂O): 1.07 (3H, d, J=7.3 Hz), 1.27 (3H, d, J=6.6 Hz), 2.15 (3H, s), 3.24 (1H, m), 3.48 (1H, dd, J=2.6 Hz and 5.9 Hz), 4.25 (2H, m), 5.22 (2H, s), 7.72 (1H, s)

EXAMPLE 47

47-a)

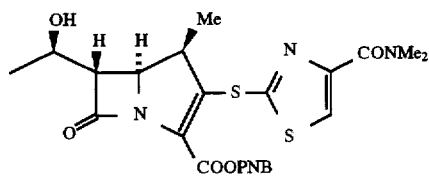

IR$_{max}$ cm$^{-1}$ (neat): 3400, 1778, 1755, 1630, 1520, 1345

$^1$H-NMR δ (CDCl$_3$): 1.10 (3H, d, J=6.6 Hz), 1.32 (3H, d, J=6.3 Hz), 3.11 (d, J=4.6 Hz, —OH), 3.12 (3H, s), 3.24 (3H, s), 3.30 (1H, dd, J=3.0 Hz and 6.3 Hz), 3.47 (1H, m), 4.26 (2H, m), 5.30 (1H, d, J=13.9 Hz), 5.53 (1H, d, J=13.9 Hz), 7.66 (2H, d, J=8.9 Hz), 7.99 (1H, s), 8.23 (2H, d, J=8.9 Hz)

47-b)

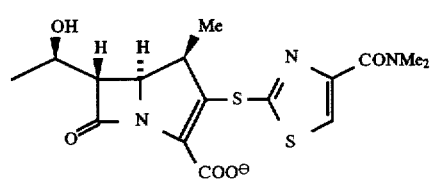

UV$_{max}$ nm (H$_2$O): 310, 250 (sh)

IR$_{max}$ cm$^{-1}$ (KBr): 3420, 1759, 1612, 1392

$^1$H-NMR δ (D$_2$O): 1.10 (3H, d, J=7.3 Hz), 1.29 (3H, d, J=6.3 Hz), 3.11 (3H, s), 3.12 (3H, s), 3.30 (1H, m), 3.50 (1H, dd, J=2.6 Hz and 5.9 Hz), 4.26 (2H, m), 8.02 (1H, s)

EXAMPLE 48

48-a)

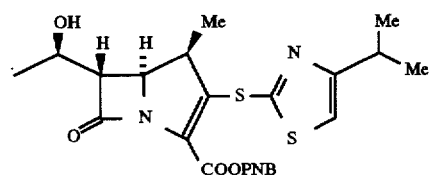

IR$_{max}$ cm$^{-1}$ (neat): 3500, 1778, 1702, 1522, 1345

$^1$H-NMR δ (CDCl$_3$): 1.09 (3H, d, J=7.6 Hz), 1.32 (9H, m), 3.13 (1H, m), 3.28 (1H, dd, J=3.0 Hz and 6.9 Hz), 3.46 (1H, m), 4.25 (2H, m), 5.29 (1H, J=13.5 Hz), 5.53 (1H, d, J=13.5 Hz), 7.02 (1H, s), 7.67 (2H, d, J=8.7 Hz), 8.24 (2H, d, J=8.7 Hz)

48-b)

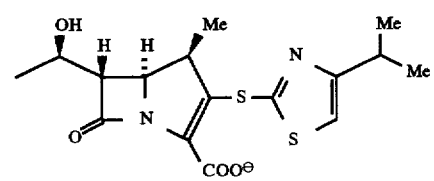

UV$_{max}$ nm (H$_2$O): 309, 267 (sh)

IR$_{max}$ cm$^{-1}$ (KBr): 3388, 1752, 1603, 1394

$^1$H-NMR δ (D$_2$O): 1.07 (3H, d, J=7.3 Hz), 1.27 (3H, d, J=6.3 Hz), 1.29 (6H, d, J=6.9 Hz), 3.16 (2H, m), 3.46 (1H, dd, J=2.6 Hz and 5.9 Hz), 4.26 (2H, m), 7.34 (1H, s)

EXAMPLE 49

49-a)

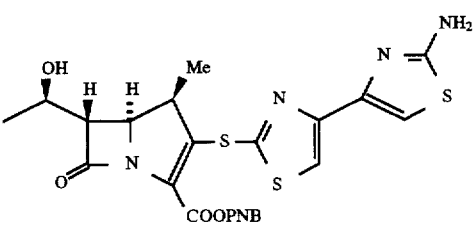

IR$_{max}$ cm$^{-1}$ (KBr): 3511, 1774, 1522, 1343

$^1$H-NMR δ (CDCl$_3$): 1.12 (3H, d, J=7.6 Hz), 1.34 (3H, d, J=6.3 Hz), 3.30 (1H, dd, J=3.0 Hz and 6.9 Hz), 3.59 (1H, m), 4.30 (2H, m), 5.29 (1H, d, J=13.2 Hz), 5.54 (1H, d, J=13.2 Hz), 7.19 (1H, s), 7.36 (1H, s), 7.68 (2H, d, J=8.9 Hz), 8.24 (2H, d, J=8.9 Hz)

49-b)

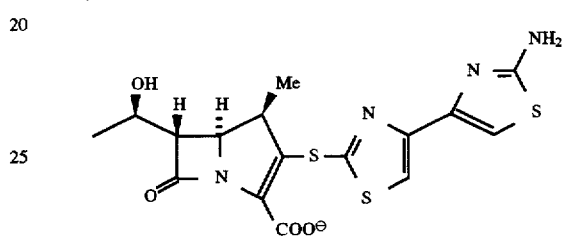

UV$_{max}$ nm (H$_2$O): 323 (sh), 280

IR$_{max}$ cm$^{-1}$ (KBr): 3334, 1755, 1600, 1527, 1394

$^1$H-NMR δ (D$_2$O): 1.10 (3H, d, J=7.3 Hz), 1.26 (3H, d, J=6.3 Hz), 3.32 (1H, m), 3.49 (1H, dd, J=3.0 Hz and 5.9 Hz), 4.28 (2H, m), 7.07 (1H, s), 7.76 (1H, s)

EXAMPLE 50

50-a)

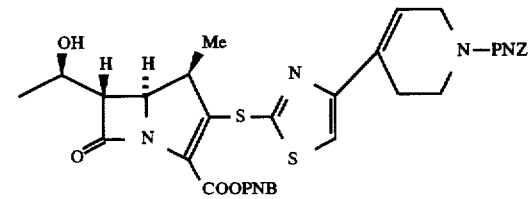

$^1$H-NMR δ (CDCl$_3$): 1.12 (3H, d, J=7.3 Hz), 1.33 (3H, d, J=6.3 Hz), 2.54 (2H, m), 3.30 (1H, dd, J=2.6 Hz and 6.9 Hz), 3.59 (1H, m), 3.75 (2H, m), 4.27 (2H, m), 5.27 (2H, s), 5.30 (1H, d, J=13.9 Hz), 5.52 (1H, d, J=13.9 Hz), 6.67 (1H, br.s), 7.13 (1H, s), 7.53 (2H, d, J=8.9 Hz), 7.67 (2H, d, J=8.9 Hz), 8.23 (4H, m)

50-b)

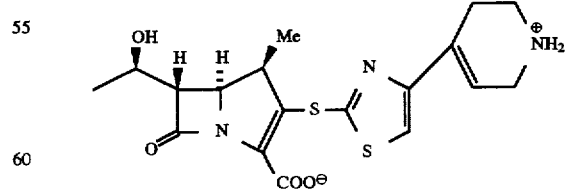

UV$_{max}$ nm (H$_2$O): 313, 247 (sh)

IR$_{max}$ cm$^{-1}$ (KBr): 3388, 1762, 1599, 1388

$^1$H-NMR δ (D$_2$O): 1.10 (3H, d, J=7.3 Hz), 1.27 (3H, d, J=6.6 Hz), 2.83 (2H, m), 3.32 (1H, m), 3.51 (3H, m), 3.93 (2H, m), 4.26 (2H, m), 6.53 (1H, br.s), 7.61 (1H, s)

EXAMPLE 51

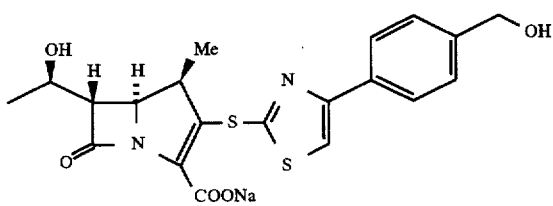

UV$_{max}$ nm (H$_2$O): 316, 265

IR$_{max}$ cm$^{-1}$ (KBr): 3434, 1752, 1598, 1394

$^1$H-NMR δ (d$_2$O): 1.10 (3h, d, J=6.9 hz), 1.27 (3H, d, J=6.6 Hz), 3.30 (1H, m), 3.48 (1H, dd, J=2.6 Hz and 5.9 Hz), 4.24 (2h, m), 4.70 (1H, s), 7.50 (2H, d, J=8.3 Hz), 7.85 (2H, d, J=8.3 Hz), 7.91 (1H, s)

EXAMPLE 52

52-a)

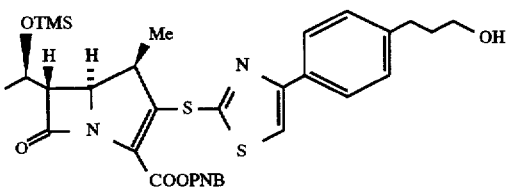

IR$_{max}$ cm$^{-1}$ (neat): 3369, 1779, 1732, 1668, 1520, 1347

$^1$H-NMR δ (CDCl$_3$): 0.13 (9H, s), 1.22 (3H, d, J=6.9 Hz), 1.35 (3H, d, J=6.3 Hz), 1.93 (2H, m), 3.33 (1H, dd, J=2.6 Hz and 6.6 Hz), 3.40–4.30 (7H, m), 5.23 (1H, d, J=13.9 Hz), 5.36 (1H, d, J=13.9 Hz), 7.10–7.40 (5H, m), 7.55 (2H, d, J=8.9 Hz), 8.13 (2H, d, J=8.9 Hz)

52-b)

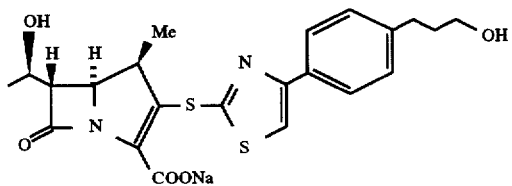

UV$_{max}$ nm (H$_2$O): 315, 263

IR$_{max}$ cm$^{-1}$ (kbr): 3406, 1756, 1603, 1394

$^1$H-NMR δ (D$_2$O): 1.09 (3H, d, J=7.3 Hz), 1.25 (3H, d, J=6.3 Hz), 1.87 (2H, m), 2.74 (2H, m), 3.31 (1H, m), 3.47 (1H, dd, J=2.6 Hz and 5.9 Hz), 3.64 (2H, m), 4.24 (2H, m), 7.39 (2H, d, J=8.3 Hz), 7.79 (2H, d, J=8.3 Hz), 7.86 (1H, s)

We claim:

1. A compound of the formula [1]:

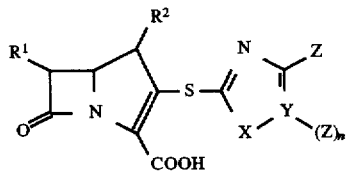

[1]

wherein R$^1$ is a lower alkyl group or a lower alkyl group substituted by a hydroxy group, R$^2$ is a hydrogen atom or a lower alkyl group, X is an oxygen atom, a sulfur atom or NH, Y is a nitrogen atom or a carbon atom, n is 0 when Y is a nitrogen atom, or n is 1 when Y is a carbon atom, Zs are each independently a) a hydrogen atom; b) R$^a$ (R$^a$ is a lower alkyl group, a substituted lower alkyl group or a substituted lower alkenyl group); c) A (A is an aryl group, a substituted aryl group or a 5- to 6-membered cyclic amino group); d) —OH or —OP$^a$ (P$^a$ is a protecting group for hydroxy group); e) —OR$^a$ (R$^a$ is the same as defined above); f) —OA (A is the same as defined above); g) —SR$^a$ (R$^a$ is the same as defined above); h) —SA (A is the same as defined above); i) —NH$_2$ or —NHP$^b$ (P$^b$ is a protecting group for amino group); j) —NHR$^a$, —N(R$^b$)R$^c$ or —N(R$^a$)P$^b$ (R$^a$ and P$^b$ are the same as defined above, R$^b$ and R$^c$ are a lower alkyl group or a substituted lower alkyl group, or R$^b$ and R$^c$ may combine together with the nitrogen atom to form a 5- to 6-membered heterocyclic group, said heterocyclic group optionally containing other 1 or 2 heteroatoms selected from an oxygen atom, a sulfur atom and a nitrogen atom, and having optionally a substituent); k) —NHA or —N(A)P$^b$ (A and P$^b$ are the same as defined above); l) —N(R$^a$)A (A and R$^a$ are the same as defined above); m) —CONH$_2$; n) —CONHRa, —CON(R$^b$)R$^c$(R$^a$,R$^b$ and R$^c$ are the same as defined above); o) —CONHA (A is the same as defined above); p) —CON(R$^a$)A (A and R$^a$ are the same as defined above); q) —CONHC(NH)NH$_2$ or —CONHC(NP$^b$)NHP$^b$ (P$^b$ is the same as defined above); r) —COOH or —COOP$^c$ (P$^c$ is a protecting group for carboxyl group); s) —COOR$^a$ (R$^a$ is the same as defined above); t) —COOA (A is the same as defined above); u) —COR$^a$ (R$^a$ is the same as defined above); v) —COA (A is the same as defined above); w) a halogen atom; or x) a cyano group, or a pharmaceutically acceptable salt thereof or a non-toxic ester thereof.

2. The compound according to claim 1, wherein X is a sulfur atom, or a pharmaceutically acceptable salt thereof or a non-toxic ester thereof.

3. The compound according to claim 1, which is a compound of the formula [1-a]:

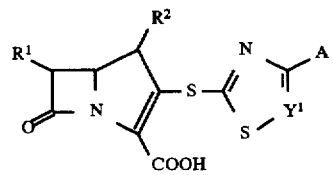

[1-a]

wherein R$^1$, R$^2$ and A are the same as defined above, and Y$^1$ is N or CH, or a pharmaceutically acceptable salt thereof, or a non-toxic ester thereof.

4. The compound according to claim 3, wherein R$^1$ is a 1-(R)-hydroxyethyl group, or a pharmaceutically acceptable salt thereof or a non-toxic ester thereof.

5. The compound according to claim 4, wherein Y$^1$ is CH, or a pharmaceutically acceptable salt thereof or a non-toxic ester thereof.

6. A process for producing a β-lactam compound of the formula [1]:

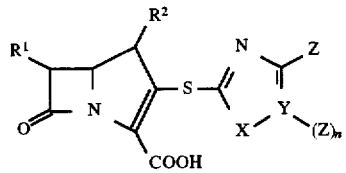

[1]

wherein $R^1$ is a lower alkyl group or a lower alkyl group substituted by a hydroxy group, $R^2$ is a hydrogen atom or a lower alkyl group, X is an oxygen atom, a sulfur atom or NH, Y is a nitrogen atom or a carbon atom, n is 0 when Y is a nitrogen atom, or n is 1 when Y is a carbon atom, Zs are each independently a) a hydrogen atom; b) $R^a$ ($R^a$ is a lower alkyl group or a substituted lower alkyl group); c) A (A is an aryl group or a substituted aryl group); d) —OH or $OP^a$ ($P^a$ is a protecting group for hydroxy group); e) —$OR^a$ ($R^a$ is the same as defined above); f) —OA (A is the same as defined above); g) —$SR^a$ ($R^a$ is the same as defined above); h) —SA (A is the same as defined above); i) —$NH_2$ or —$NHP^b$ ($P^b$ is a protecting group for amino group); j) —$NHR^a$, —$N(R^b)R^c$ or —$N(R^a)P^b$ ($R^a$ and $P^b$ are the same as defined above, $R^b$ and $R^c$ are a lower alkyl group or a substituted lower alkyl group, or $R^b$ and $R^c$ may combine together with the nitrogen atom to form a 5- to 6-membered heterocyclic group, said heterocyclic group optionally containing other 1 or 2 heteroatoms selected from an oxygen atom, a sulfur atom and a nitrogen atom, and having optionally a substituent); k) —NHA or —$N(A)P^b$ (A and $P^b$ are the same as defined above); l) —$N(R^a)A$ (A and $R^a$ are the same as defined above); m) —$CONH_2$; n) —$CONHR^a$, —$CON(R^b)R^c$ ($R^a$, $R^b$ and $R^c$ are the same as defined above); o) —CONHA (A is the same as defined above); p) —CON($R^a$)A (A and $R^a$ are the same as defined above); q) —$CONHC(NH)NH_2$ or —$CONHC(NP^b)NHP^b$ ($P^b$ is the same as defined above); r) —COOH or —COOPC ($P^c$ is a protecting group for carboxyl group); s) —$COOR^a$ ($R^a$ is the same as defined above); t) —COOA (A is the same as defined above); u) —$COR^a$ ($R^a$ is the same as defined above); v) —COA (A is the same as defined above); w) a halogen atom; or x) a cyano group, or a pharmaceutically acceptable salt thereof or a non-toxic ester thereof, which comprises reacting a compound of the formula [2]:

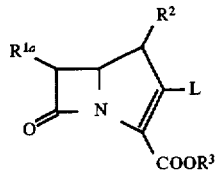

[2]

wherein $R^2$ is the same as defined above, $R^1a$ is a lower alkyl group, a lower alkyl group substituted by a hydroxy group, or a lower alkyl group substituted by a hydroxy group protected by a protecting group, $R^3$ is a protecting group for carboxyl group, L is an active ester of hydroxy group, with a compound of the formula [3]:

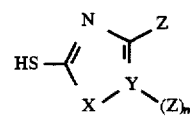

[3]

wherein X, Y, Z and n are the same as defined above, in the presence of a base, or reacting the compound of the formula [2] with a thiolate salt of the compound of the formula [3], to give a compound of the formula [4]:

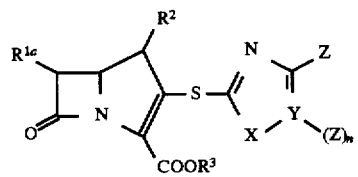

[4]

wherein $R^{1a}$, $R^2$, $R^3$, X, Y, Z and n are the same as defined above, followed by removing the protecting group for hydroxy group for $R^{1a}$ and/or removing the protecting group for carboxyl group represented by $R^3$.

7. The compound according to claim 1, wherein the 5- to 6-membered heterocyclic group formed when $R^b$ and $R^c$ combined together with the nitrogen atom is selected from the group consisting of aziridinyl, azetidinyl, pyrrolidinyl, piperidinyl, piperazinyl, homopiperazinyl, imidazolinyl, imidazolidinyl, morpholinyl and thiamorpholinyl.

* * * * *